(12) United States Patent
Hatakeyama et al.

(10) Patent No.: US 7,232,641 B2
(45) Date of Patent: Jun. 19, 2007

(54) POLYMERIZABLE COMPOUND, POLYMER, POSITIVE-RESIST COMPOSITION, AND PATTERNING PROCESS USING THE SAME

(75) Inventors: Jun Hatakeyama, Niigata (JP); Yuji Harada, Niigata (JP); Yoshio Kawai, Niigata (JP)

(73) Assignee: Shin-Etsu Chemical Co., Ltd., Tokyo (JP)

( * ) Notice: Subject to any disclaimer, the term of this patent is extended or adjusted under 35 U.S.C. 154(b) by 107 days.

(21) Appl. No.: 10/953,334

(22) Filed: Sep. 30, 2004

(65) Prior Publication Data

US 2005/0079446 A1    Apr. 14, 2005

(30) Foreign Application Priority Data

Oct. 8, 2003    (JP) .............................. 2003-350145

(51) Int. Cl.
*G03F 7/039*    (2006.01)
*G03F 7/38*    (2006.01)

(52) U.S. Cl. .................... 430/270.1; 430/330; 430/326

(58) Field of Classification Search .................... None
See application file for complete search history.

(56) References Cited

U.S. PATENT DOCUMENTS

| | | | |
|---|---|---|---|
| 4,491,628 A | 1/1985 | Ito et al. | |
| 5,843,624 A | 12/1998 | Houlihan et al. | |
| 6,030,747 A * | 2/2000 | Nakano et al. | 430/270.1 |
| 6,403,280 B1 * | 6/2002 | Yamahara et al. | 430/270.1 |
| 2002/0051936 A1 * | 5/2002 | Harada et al. | 430/270.1 |
| 2003/0219678 A1 * | 11/2003 | Harada et al. | 430/270.1 |
| 2003/0235781 A1 * | 12/2003 | Shida et al. | 430/270.1 |
| 2005/0079440 A1 * | 4/2005 | Hatakeyama et al. | 430/270.1 |

FOREIGN PATENT DOCUMENTS

JP    A 63-27829    2/1988

(Continued)

OTHER PUBLICATIONS

Hiroshi Ito et al.; "Dissolution/swelling behavior of cycloolefin polymers in aqueous base"; In Advances in Resist Technology and Processing XVII; Proceedings of SPIE vol. 3999; 2000; pp. 2-12.

(Continued)

*Primary Examiner*—Cynthia Hamilton
(74) *Attorney, Agent, or Firm*—Oliff & Berridge, PLC

(57) ABSTRACT

The present invention provides a polymer which has at least one or more of a repeating unit represented by a following general formula (1a), a repeating unit represented by a following general formula (2a) and a repeating unit represented by a following general formula (3b), and a repeating unit represented by a following general formula (1c), and a positive resist composition which contains as a base resin the polymer. Thereby, there can be provided a positive-resist composition having high sensitivity and high resolution in exposure with a high energy beam, wherein line edge roughness is small since swelling at the time of development is suppressed, and the residue after development is few

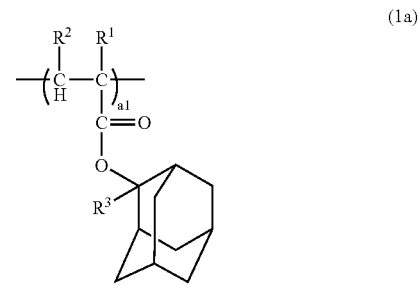

(1a)

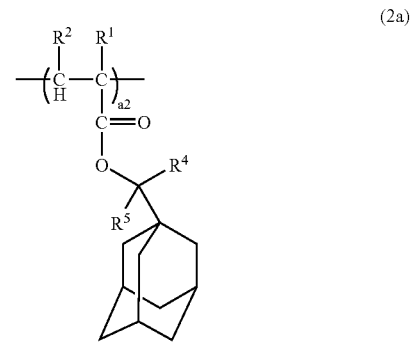

(2a)

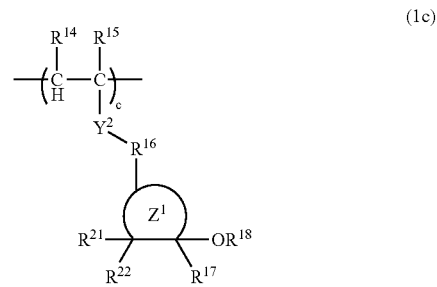

(1c)

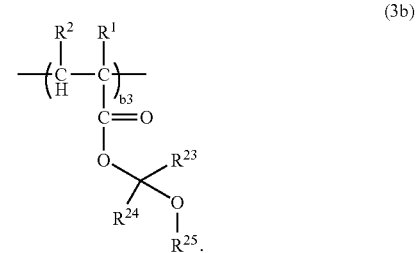

(3b)

20 Claims, 2 Drawing Sheets

FOREIGN PATENT DOCUMENTS

| | | |
|---|---|---|
| JP | B2 2-27660 | 6/1990 |
| JP | A 9-73173 | 3/1997 |
| JP | A 9-90637 | 4/1997 |
| JP | A 9-230595 | 9/1997 |
| JP | A 10-10739 | 1/1998 |
| JP | A 2000-26446 | 1/2000 |
| JP | A 2000-159758 | 6/2000 |
| WO | WO 97/33198 | 9/1997 |
| WO | WO 2004050725 A1 * | 6/2004 |

OTHER PUBLICATIONS

H Ito et al.; "Fluoropolymer Resists: Progress and Properties"; Journal of Photopolymer Science and Technology; vol. 16, No. 4; 2003; pp. 523-536.

Cheng-Ping Qian et al.; Generation and Use of Lithium Pentafluoropropen-2-Olate: 4-Hydroxy-1, 1, 1,3,3-Pentafluoro-2-Hexanone Hydrate (2,2,4-Hexanetriol, 1,1,1,3,3-pentafluoro-from 1-Propen-2-ol, 1,1,3,3,3-pentafluoro-, lithium salt); Organic Synthesis; vol. 76; 1998; pp. 151-158.

* cited by examiner

POLYMERIZABLE COMPOUND, POLYMER, POSITIVE-RESIST COMPOSITION, AND PATTERNING PROCESS USING THE SAME

BACKGROUND OF THE INVENTION

1. Field of the Invention

The present invention relates to a positive-resist composition, especially to a chemically amplified positive-resist composition, suitable as a micropatterning material, especially for the VLSI manufacture, or for manufacture of a photomask pattern, which shows a high alkali dissolution-rate contrast before and after exposure, high sensitivity and high resolution, a reduced line edge roughness, and an outstanding etching resistance in exposure with a high energy beam.

2. Description of the Related Art

In recent years, with a tendency that integration and speed have become higher in LSI, a tendency that a pattern rule becomes finer progresses rapidly. In the background that the tendency that a pattern becomes finer has progressed quickly, there are a tendency that NA of a projection lens has become higher, improvement in resist performance, and a tendency that a wavelength has become shorter. Especially a tendency that a wavelength becomes shorter from i line (365 nm) to KrF (248 nm) causes a big change, and thus mass production of a device with 0.18 μm rule is also made possible. The chemically amplified positive-resist composition in which an acid is used as a catalyst (for example, see Japanese Patent Publication No. 2-27660 and Japanese Patent Application Laid-open (KOKAI) No. 63-27829) has an outstanding feature in the tendency that resolution and sensitivity of resist become higher, and thus has become a main resist composition especially for deep-ultraviolet lithography.

The resist composition for KrF excimer lasers has began to be used generally for a 0.3-micron process, and it has also been began to be applied to mass-production of 0.18-micron rule via a 0.25-micron rule. Furthermore, examination of a 0.15 micron rule has also been started, and the tendency that a pattern becomes finer is accelerated increasingly. It is expected that a design rule should be 0.13 μm or less with a tendency that a wavelength becomes shorter from a KrF excimer laser to an ArF excimer laser (193 nm). However, it was hard to use novolak and polyvinyl phenol resin which have been used conventionally as a base resin for resist, since it has a quite strong absorption near the wavelength of 193 nm. Then, aliphatic resins such as acrylic resins or cycloolefin resins have been examined to ensure transparency and a required dry etching resistance (for example, see Japanese Patent Application Laid-open (KOKAI) No. 9-73173, Japanese Patent Application Laid-open (KOKAI) No. 10-10739, Japanese Patent Application Laid-open (KOKAI) No. 9-230595, and International publication No. 97/33198).

Among them, the resist based on (meth)acrylic base resin with a high resolution has been examined. As (meth)acrylic resin, the combination of the (meth)acrylic which has methyl adamantane ester as an acid labile group unit and the (meth)acrylic which has an ester of a lactone ring as an adhesion group unit has been proposed (for example, see Japanese Patent Application Laid-open (KOKAI) No. 9-90637). Furthermore, norbornyl lactone has been proposed as an adhesion group by which an etching resistance is reinforced (for example, see Japanese Patent Application Laid-open (KOKAI) No. 2000-26446 and Japanese Patent Application Laid-open (KOKAI) No. 2000-159758).

Reduction of line edge roughness and reduction of residue after development are mentioned as one of the problems in ArF lithography. Swelling at the time of development is mentioned as one of the causes for line edge roughness. Although polyhydroxy styrene used as a resist for KrF lithography is hardly swelled since phenol thereof is a weakly acidic group and has a moderate alkali solubility, swelling at the time of development is easily caused in the polymer containing a highly hydrophobic alicyclic group, since it is dissolved with a carboxylic acid with high acidity.

Here, the amount of swelling during development has been reported by measurement of the development characteristics of the resist according to the QCM (Quartz Crystal Microbalance) method (for example, see Proc. SPIE Vol. 3999 p2 (2000)). Although swelling of the film during development cannot be observed by a conventional optical interference thickness-measurement method, it is possible to observe increase in weight of the film by swelling according to the QCM method, since the weight change of a film is measured electrically. In the reference, swelling of the ArF resist based on cycloolefin polymer is disclosed. Significant swelling is observed especially in the case that a carboxylic acid is used as an adhesion group.

SUMMARY OF THE INVENTION

The present invention has been made in order to solve such problems. The object of the present invention is to provide a positive-resist composition showing high sensitivity and high resolution in exposure with a high energy beam, reduced line edge roughness due to suppressed swelling at the time of development, and reduced residues after development.

To achieve the above mentioned object, the present invention provides a polymerizable compound represented by a following general formula (1),

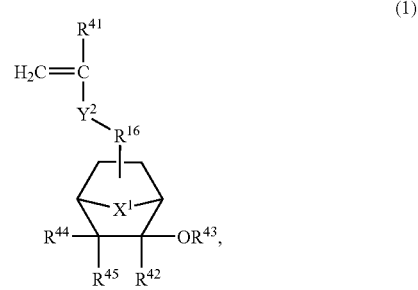

(1)

wherein $R^{41}$ is a hydrogen atom or a methyl group, $R^{42}$ is a fluorine atom or a trifluoro methyl group, $R^{43}$ is a hydrogen atom or a monovalent acyl group, $R^{44}$ and $R^{45}$ each independently represents a hydrogen atom or a fluorine atom, $R^{16}$ is a single bond or a linear or branched alkylene group having 1–4 carbon atoms, $X^1$ is any one of a methylene group, an ethylene group, an oxygen atom and a sulfur atom, and $Y^2$ is —O— or —C(=O)—O—.

The present invention provides a polymer which has at least one or more of a repeating unit represented by a following general formula (1a), a repeating unit represented by a following general formula (2a) and a repeating unit represented by a following general formula (3b), and a repeating unit represented by a following general formula (1c),

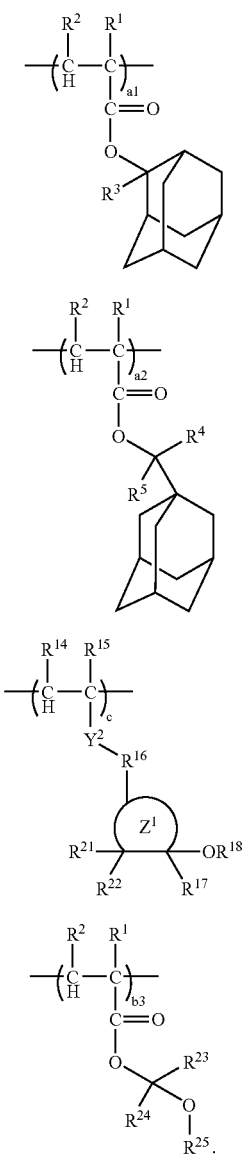

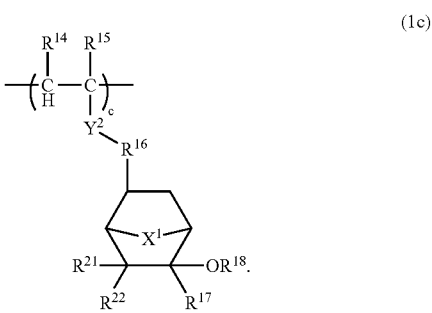

wherein $R^1$ represents any one of a hydrogen atom, a methyl group and —$CH_2CO_2R^6$, $R^2$ represents any one of a hydrogen atom, a methyl group and —$CO_2R^6$, $R^1$ and $R^2$ in the repeating units (1a) and (2a) may be the same or different, $R^3$ to $R^5$ each independently represent a monovalent hydrocarbon group having 1–15 carbon atoms which may contain a hetero atom, $R^6$ represents a hydrogen atom or a linear, branched or cyclic alkyl group having 1–15 carbon atoms, $R^{15}$ represents any one of a hydrogen atom, a methyl group and —$CH_2CO_2R^6$, $R^{14}$ represents any one of a hydrogen atom, a methyl group and —$CO_2R^6$, $R^{16}$ represents a single bond or a linear or branched alkylene group having 1–4 carbon atoms, $R^{17}$ represents a fluorine atom or a trifluoro methyl group, $R^{18}$ represents any one of a hydrogen atom, an acyl group having 1–10 carbon atoms and an acid labile group, $R^{21}$ and $R^{22}$ each independently represent a hydrogen atom or a fluorine atom, $R^{23}$ and $R^{24}$ each independently represent a hydrogen atom or a linear or branched alkyl group having 1–6 carbon atoms, $R^{25}$ is a linear, branched or cyclic alkyl group having 1–20 carbon atoms, $Y^2$ is —O— or —C(=O)—O—, $Z^1$ is a bridged cyclic hydrocarbon group having 4–10 carbon atoms, which may have —O— and/or —S—, and a1, a2, c, and b3 fall within the range that $0 \leq a1 \leq 0.8$, $0 \leq a2 \leq 0.8$, $0 \leq b3 \leq 0.8$, $0.1 \leq a1+a2+b3 \leq 0.8$, and $0 < c \leq 0.9$.

In this case, it is desirable that the repeating unit represented by the general formula (1c) is a repeating unit represented by a following general formula, (1c)

wherein $R^{14}$, $R^{15}$, $R^{16}$, $R^{17}$, $R^{18}$, $R^{21}$, $R^{22}$, $Y^2$, a same as mentioned above, and $X^1$ is any one of a methylene group, an ethylene group, an oxygen atom and a sulfur atom.

Such a polymer of the present invention can be easily obtained, for example, by polymerizing the novel polymerizable compound represented by the above-mentioned general formula (1), and any one or more compounds of the compound for obtaining the repeating unit represented by the above-mentioned general formula (1a), the compound for obtaining the repeating unit represented by the above-mentioned general formula (2a) and the compound for obtaining the repeating unit represented by the above-mentioned general formula (3b). And the positive-resist composition which contains the above-mentioned polymer as a base resin shows a sharply high alkali dissolution-rate contrast before and after exposure in exposure with a high energy beam, shows a high sensitivity and a high resolution, and shows a reduced line edge roughness since swelling at the time of development is suppressed. Furthermore, etch residues thereof is few, and etching resistance thereof is excellent. Therefore, since it has these characteristics, practicality is very high, and it is suitable for the VLSI manufacture, or for micropatterning material in production of a photomask pattern.

And it is desirable that the positive-resist composition of the present invention further contains an organic solvent and an acid generator to serve as a chemically amplified resist composition.

As described above, if the polymer of the present invention is used as a base resin and an organic solvent and an acid generator are further blended therein, there can be obtained the chemically amplified positive-resist composition, which shows very high sensitivity since a dissolution rate of the above-mentioned polymer in a developer in an exposed area is accelerated by an acid catalysis, and is very suitable as a micropatterning material for the VLSI manufacture or the like which has been demanded in recent years.

In this case, the positive-resist composition of the present invention may further contains a dissolution inhibitor.

By blending a dissolution inhibitor in the positive-resist composition as described above, the difference of the dissolution rate in the exposed area and the non-exposed area can be enlarged further, and a resolution can be raised further.

Moreover, in the positive-resist composition of the present invention, a basic compound and/or a surfactant may be further blended as an additive.

For example, a diffusion rate of an acid in a resist film can be suppressed and a resolution can be further improved, by adding a basic compound as descried above, and an application property of a resist composition can be further improved or controlled by adding a surfactant.

Such a resist composition of the present invention can be used for a process of forming a pattern on a semiconductor substrate, a mask substrate, or the like by performing, at least, a step of applying the resist composition to the substrate, a step of exposing the applied resist composition with a high energy beam after heat-treatment, and a step of developing the exposed resist composition by using a developer.

Of course, development may be conducted after conducting the heat treatment after exposure, and other various processes, such as an etching process, a resist removing process, a cleaning process or the like may be performed.

In this case, the above-mentioned high energy beam may have a wavelength in the range of 180 nm–200 nm.

The resist composition which contains the polymer of the present invention as a base resin can be suitably used especially in exposure with a high energy beam with a wavelength in the range of 180 nm–200 nm, and sensitivity is excellent at the exposure wavelength in this range.

As explained above, the present invention provides a polymer obtained by copolymerizing a monomer which is an ester having adamantane with an acid leaving property and/or a monomer which is an ester having an acetal type acid leaving group, and a monomer which is a compound for obtaining a repeating unit having a substituted or unsubstituted alcohol having a fluorinated alkyl group or a fluorine atom at an α position. By blending this polymer as a base resin in the resist composition, there is provided the material which shows high sensitivity and high resolution, a reduced small line edge roughness, reduced residues after development, and suppression of swelling during development measured according to QCM method or the like. Therefore, it is possible to provide a positive-resist composition, such as a chemically amplified positive-resist composition suitable especially as a micropatterning material for the VLSI manufacture or for production of a photomask pattern.

Furthermore, according to the present invention, the novel polymerizable compound for obtaining such a polymer of the present invention is provided.

DETAILED DESCRIPTION OF THE PREFERRED EMBODIMENTS

Figure 1:
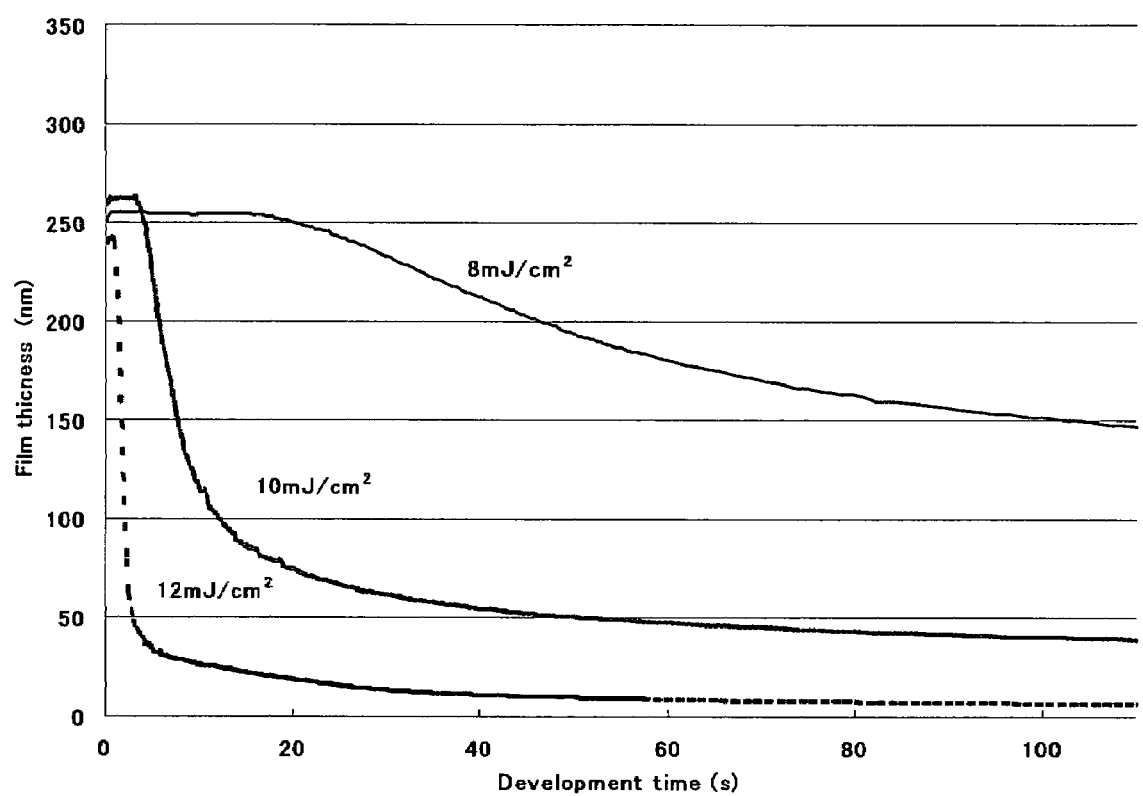
FIG. 1 is a graph which shows the result of the measurement which was performed according to the QCM method as for the resist formed by the resist composition of Example 1.

The inventors of the present invention have studied thoroughly in order to obtain a positive resist composition which shows a high sensitivity and high resolution, a reduced line edge roughness since swelling at the time of development is suppressed, and reduced residues after development in exposure with a high energy beam.

There is disclosed (meth)acrylate which has an adamantane ester with an acid leaving property, for example, in Japanese Patent Application Laid-open (KOKAI) No. 9-73173.

Moreover, examination of the resist using the hexafluoro alcohol as an object for $F_2$ lithography is performed. It has been reported that a hexafluoro alcohol has an acidity equivalent to phenol, and swelling thereof in a developer is small (J. Photopolym. Sci. Technol., Vol. 16, No. 4, p523 (2003)). Moreover, polynorbornene having a hexafluoro alcohol, and α trifluoromethyl acrylate which has pendant hexafluoro alcohol have been introduced there, and exposure characteristics in exposure with the ArF excimer laser are also introduced.

Then, the inventors have applied it, and found that a positive-resist composition which shows a high sensitivity and high resolution, reduced line edge roughness due to swelling at the time of development, and reduced residues after development can be provided by using as a base resin a polymer obtained by using a combination of (meth) acrylate which is an ester having adamantane with acid leaving property and an adhesion group which has alkali solubility such as hexafluoro alcohol. Thereby the present invention has been completed.

Namely, the polymer according to the present invention is a polymer which has at least one or more of a repeating unit represented by a following general formula (1a), a repeating unit represented by a following general formula (2a) and a repeating unit represented by a following general formula (3b), and a repeating unit represented by a following general formula (1c),

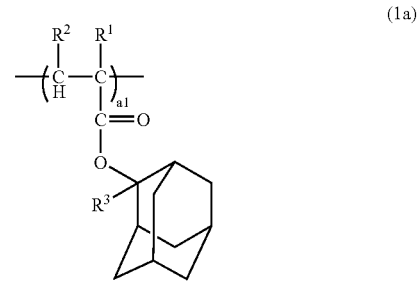

(1a)

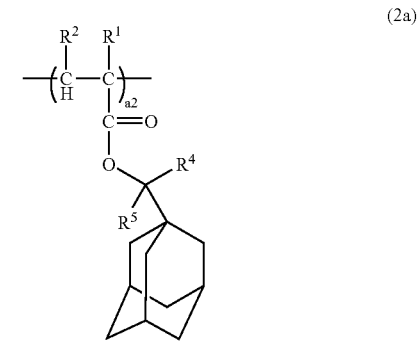

(2a)

-continued

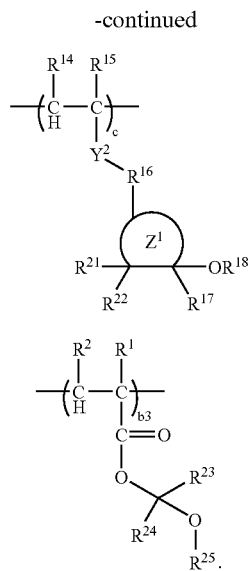

wherein $R^1$ represents any one of a hydrogen atom, a methyl group and —$CH_2CO_2R^6$, $R^2$ represents any one of a hydrogen atom, a methyl group and —$CO_2R^6$, $R^1$ and $R^2$ in the repeating units (1a) and (2a) may be the same or different, $R^3$ to $R^5$ each independently represent a monovalent hydrocarbon group having 1–15 carbon atoms which may contain a hetero atom, $R^6$ represents a hydrogen atom or a linear, branched or cyclic alkyl group having 1–15 carbon atoms, $R^{15}$ represents any one of a hydrogen atom, a methyl group and —$CH_2CO_2R^6$, $R^{14}$ represents any one of a hydrogen atom, a methyl group and —$CO_2R^6$, $R^{16}$ represents a single bond or a linear or branched alkylene group having 1–4 carbon atoms, $R^{17}$ represents a fluorine atom or a trifluoro methyl group, $R^{18}$ represents any one of a hydrogen atom, an acyl group having 1–10 carbon atoms, and an acid labile group, $R^{21}$ and $R^{22}$ each independently represent a hydrogen atom or a fluorine atom, $R^{23}$ and $R^{24}$ each independently represent a hydrogen atom or a linear or branched alkyl group having 1–6 carbon atoms, $R^{25}$ is a linear, branched or cyclic alkyl group having 1–20 carbon atoms, $Y^2$ is —O— or —C(=O)—O—, $Z^1$ is a bridged cyclic hydrocarbon group having 4–10 carbon atoms, which may have —O— and/or —S—, and a1, a2, c, and b3 fall within the range that $0 \leq a1 \leq 0.8$, $0 \leq a2 \leq 0.8$, $0 \leq b3 \leq 0.8$, $0.1 \leq a1+a2+b3 \leq 0.8$, and $0 < c \leq 0.9$.

In this case, it is desirable that the repeating unit represented by the general formula (1c) is a repeating unit represented by a following general formula,

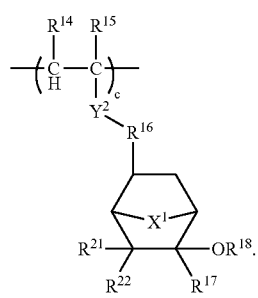

wherein $R^{14}$, $R^{15}$, $R^{16}$, $R^{17}$, $R^{18}$, $R^{21}$, $R^{22}$, $Y^2$ and c are the same as mentioned above, and $X^1$ is any one of a methylene group, an ethylene group, an oxygen atom and a sulfur atom.

The positive-resist composition which contains such a polymer of the present invention as a base resin shows, in exposure with the high energy beam, a significantly high alkali dissolution-rate contrast before and after exposure, high sensitivity and high resolution, a reduced line edge roughness due to suppression of swelling during development, reduced residues after development, and excellent etching resistance. Therefore, because of these characteristics it is suitable as a micropatterning material especially for the VLSI manufacture or for production of a photomask pattern.

Illustrative examples of the monomer which is the ester shown in the general formula (1a) or (2a) can be listed below, but it is not limited to them.

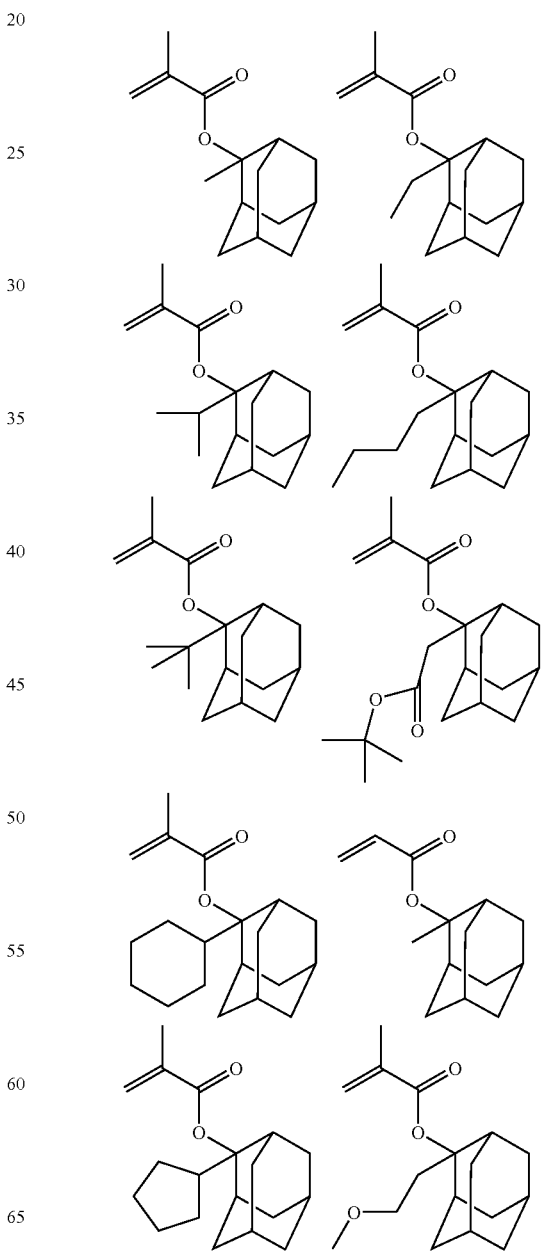

-continued

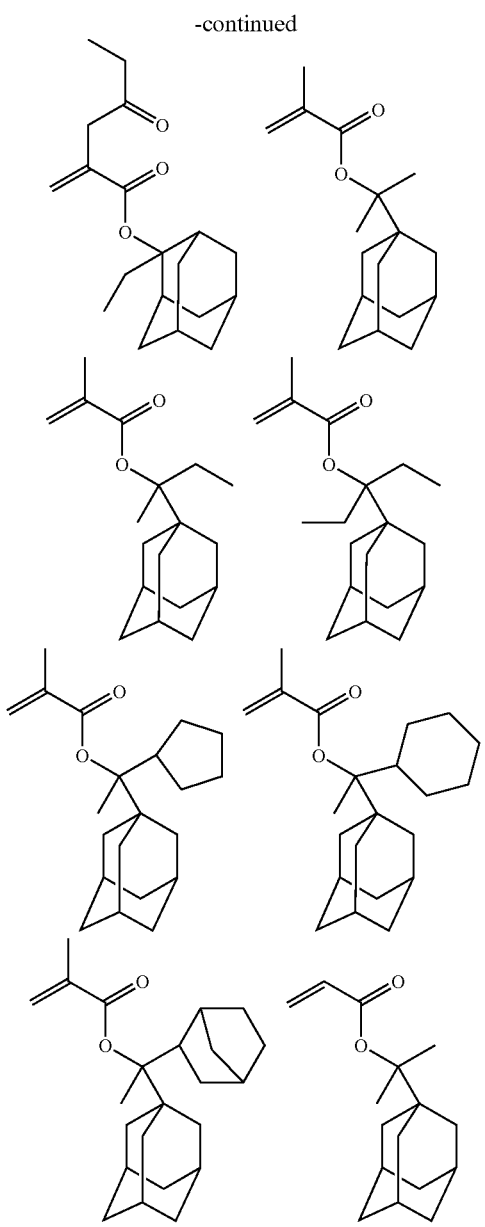

Illustrative examples of the monomer which is an ester having the acid labile group shown in the general formula (3b) can be listed below. However, it is not limited to them.

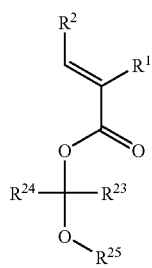

(In the formula, $R^1$, $R^2$, $R^{23}$, $R^{24}$, and $R^{25}$ are the same as those mentioned above.)

As the ester compound monomer for obtaining the repeating unit which has a substituted or unsubstituted alcohol having a fluorinated alkyl group or a fluorine atom shown in the general formula (1c), there can be mentioned a polymerizable compound represented by a following general formula (1), for example,

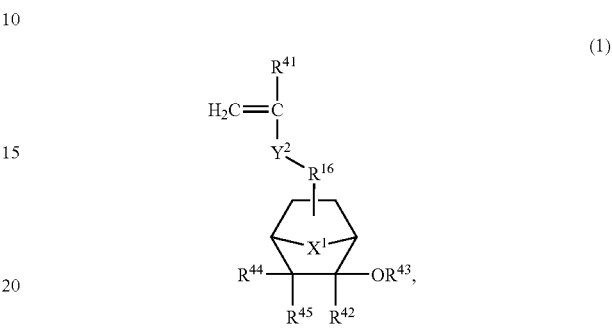

wherein $R^{41}$ is a hydrogen atom or a methyl group, $R^{42}$ is a fluorine atom or a trifluoro methyl group, $R^{43}$ is a hydrogen atom or a monovalent acyl group, $R^{44}$ and $R^{45}$ each independently represents a hydrogen atom or a fluorine atom, $R^{16}$ is a single bond or a linear or branched alkylene group having 1–4 carbon atoms, $X^1$ is any one of a methylene group, an ethylene group, an oxygen atom and a sulfur atom, and $Y^2$ is —O— or —C(=O)—O—.

The following compounds can illustratively be mentioned as the polymerizable compound represented by the above-mentioned general formula (1) and other polymerizable compounds for obtaining the repeating unit shown in the general formula (1c).

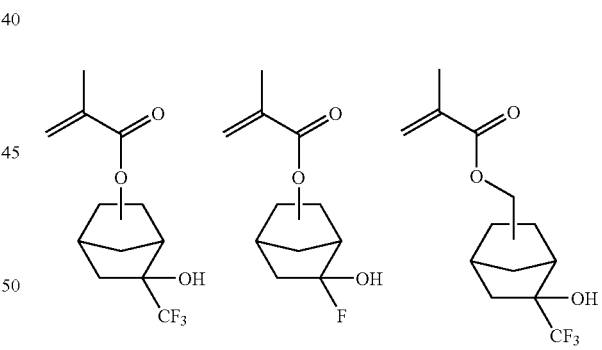

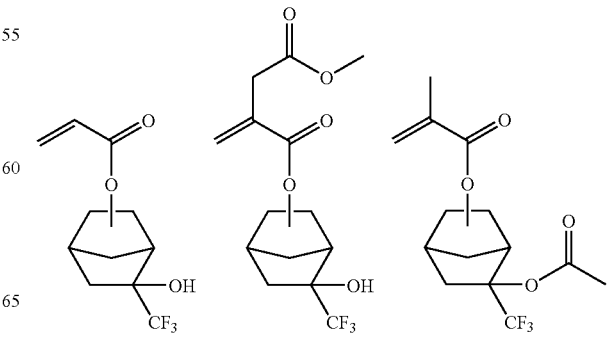

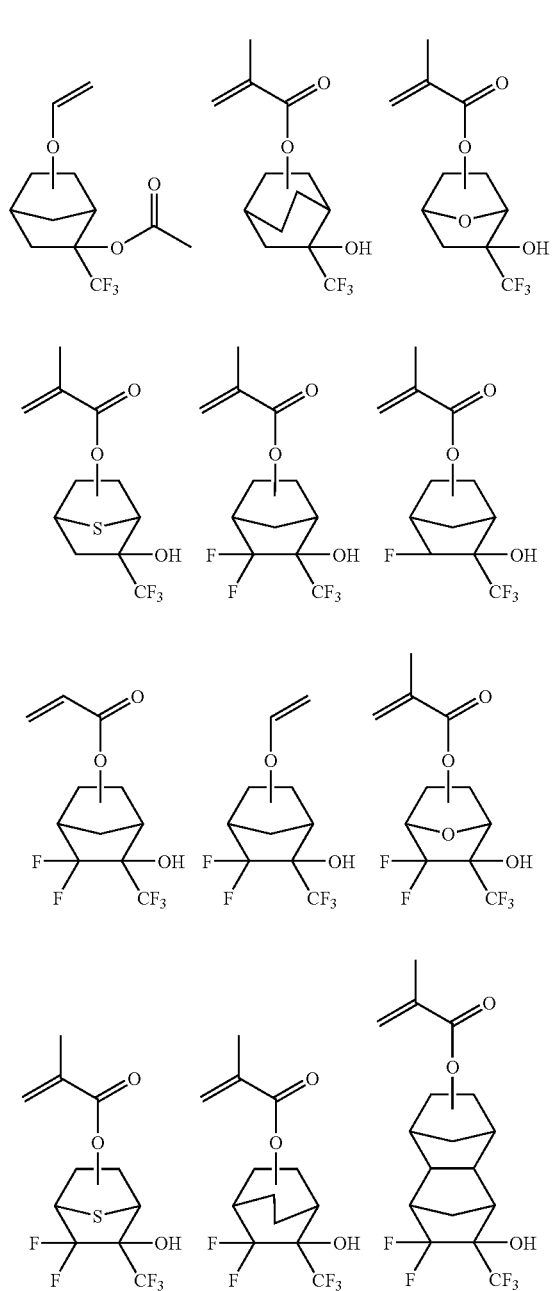

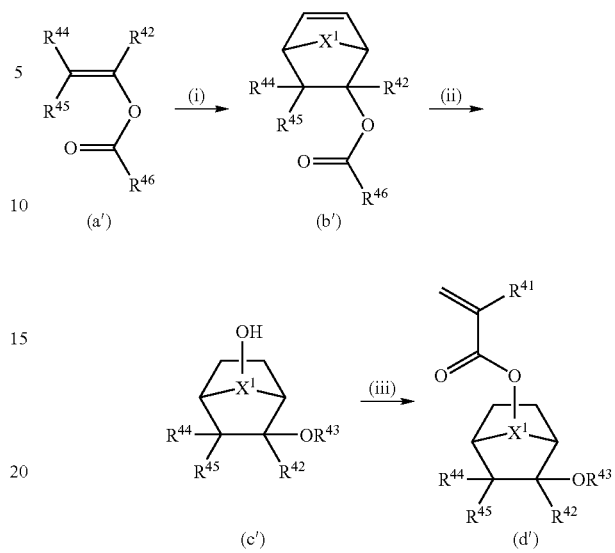

(In the formulae, $R^{41-45}$ are the same as those of the general formula (1), and $R^{46}$ is any one of a hydrogen atom, an alkyl group having 1–10 carbon atoms, and an aryl group having 6–10 carbon atoms.)

In the 1st process (i), a compound (b') is synthesized by Diels Alder reaction of a compound (a') and a diene compound. Although this reaction progresses easily under the known conditions, it is preferable that the compound (a') and the diene compound are mixed without solvent or in a solvent, and a reaction is progressed with heating or cooling if needed. Conventional methods such as recrystallization, chromatography and distillation can be used in order to isolate the intended substance from the reaction mixture.

The compound (b') is converted to a compound (c') in the 2nd process (ii). This process can also be conducted by the known method. Illustratively, it can be conducted by the method by which a trifluoroacetic acid is added to the compound (b'), and then hydrolyzed or ester exchanged, or the method by which the compound (b') is subjected to hydroboration-oxidation reaction followed by hydrolysis or ester exchange. However, it is not limited thereto. In any methods, it is possible to separate the intended substance from the reaction mixture by conventional methods such as recrystallization, chromatography, and distillation.

The 3rd process (iii) is esterification of the compound (c'). Although the reaction progresses easily under the known conditions, it is preferable to add as a raw material the compound (c'), carboxylic acid halide such as acryloyl chloride and methacryloyl chloride, and a base such as triethylamine in a solvent such as methylene chloride, sequentially or simultaneously, and be cooled if needed.

The compound (d') can also be separated from the reaction mixture according to conventional methods such as recrystallization, chromatography, and distillation.

In addition, $R^{43}$ in the monomer before polymerization represented by the general formula (1) may be the same as $R^{18}$ in the repeating unit represented by the general formula (1c) after polymerization as above. Or it may be an acetyl group before polymerization and may be converted to a hydroxy group by alkali hydrolysis after polymerization, and if necessary, a hydrogen atom of the hydroxy group may be substituted with an acid labile group thereafter.

The polymerizable compound represented by the general formula (1) can be preferably synthesized by a synthetic process shown below. However, it is not limited to the synthetic process.

The polymer of the present invention is characterized in that it is obtained by copolymerizing the monomers which are esters having adamantane with an acid leaving property represented by the formulae (1a) and (2a) and/or the monomers which are esters having an acid labile group represented by the formula (3b), and the monomer which is a compound for obtaining a repeating unit having a substituted or unsubstituted alcohol having a fluorinated alkyl group or a fluorine atom at an α position represented by the formula (1c). Furthermore, the monomer (1d) (the repeating unit d) which is an ester having an acid labile group other than those represented by the general formula (1a), (2a) and (3b) can be copolymerized.

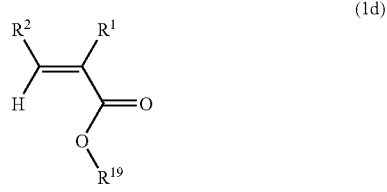

(1d)

(In the formula, $R^1$ and $R^2$ represent the same as mentioned above, and $R^{19}$ represents an acid labile group.)

Next, various acid labile groups represented by $R^{18}$ and $R^{19}$ in the general formulae (1c) and (1d) can be selected, and they may be the same or different. They may have the structure in which hydrogen of a hydroxyl group or a hydroxy group of a carboxyl group is substituted especially with the group represented by the following formula (AL10), a tertiary alkyl group having 4–40 carbon atoms represented by the following formula (AL12), an oxoalkylgroup having 4–20 carbon atoms or the like.

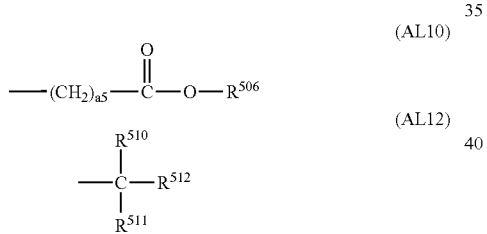

(AL10)

(AL12)

In the formula (AL10), $R^{506}$ is a linear, branched or cyclic alkyl group having 1–20 carbon atoms, and may contain hetero atoms, such as oxygen, sulfur, nitrogen, fluorine or the like. a5 is an integer of 0–10.

Illustrative examples of the compound represented by the formula (AL10) may include: tert-butoxy carbonyl group, tert-butoxy carbonyl methyl group, tert-amyloxy carbonyl group, tert-amyloxy carbonyl methyl group, 1-ethoxy ethoxy carbonyl methyl group, 2-tetrahydropyranyl oxycarbonyl methyl group, and 2-tetrahydrofuranyl oxycarbonyl methyl group, or the like, and further the substituents represented by the following general formulae (AL10)-1 to (AL10)-9.

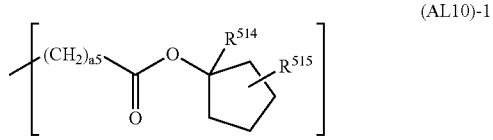

(AL10)-1

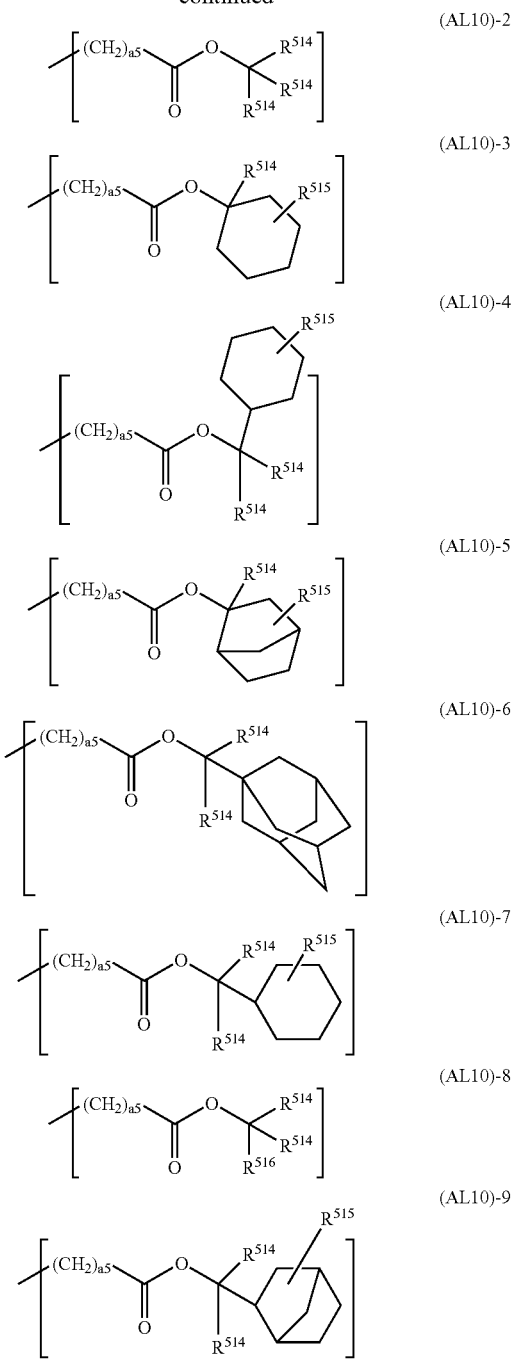

In the formulae (AL10)-1 to (AL10)-9, $R^{514}$ may be the same or different, and represents a linear, branched or cyclic alkyl group having 1–8 carbon atoms, or an aryl group or aralkyl group having 6–20 carbon atoms. $R^{515}$ does not exist or represents a linear, branched or cyclic alkyl group having 1–20 carbon atoms. $R^{516}$ represents an aryl group or an aralkyl group having 6–20 carbon atoms.

Further examples of the acid labile group represented by $R^{18}$ and $R^{19}$ in the general formulae (1c) and (1d) may include groups represented by the following general formulae (AL11)-1 to (AL11)-19, (AL11)-24 to (AL11)-33.

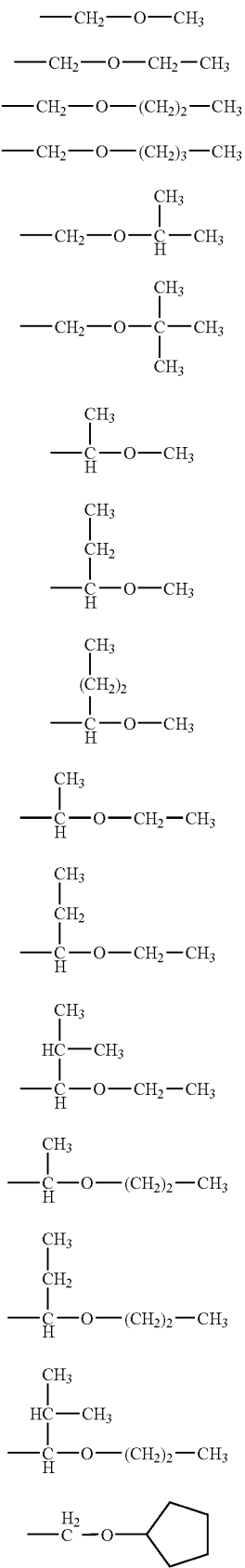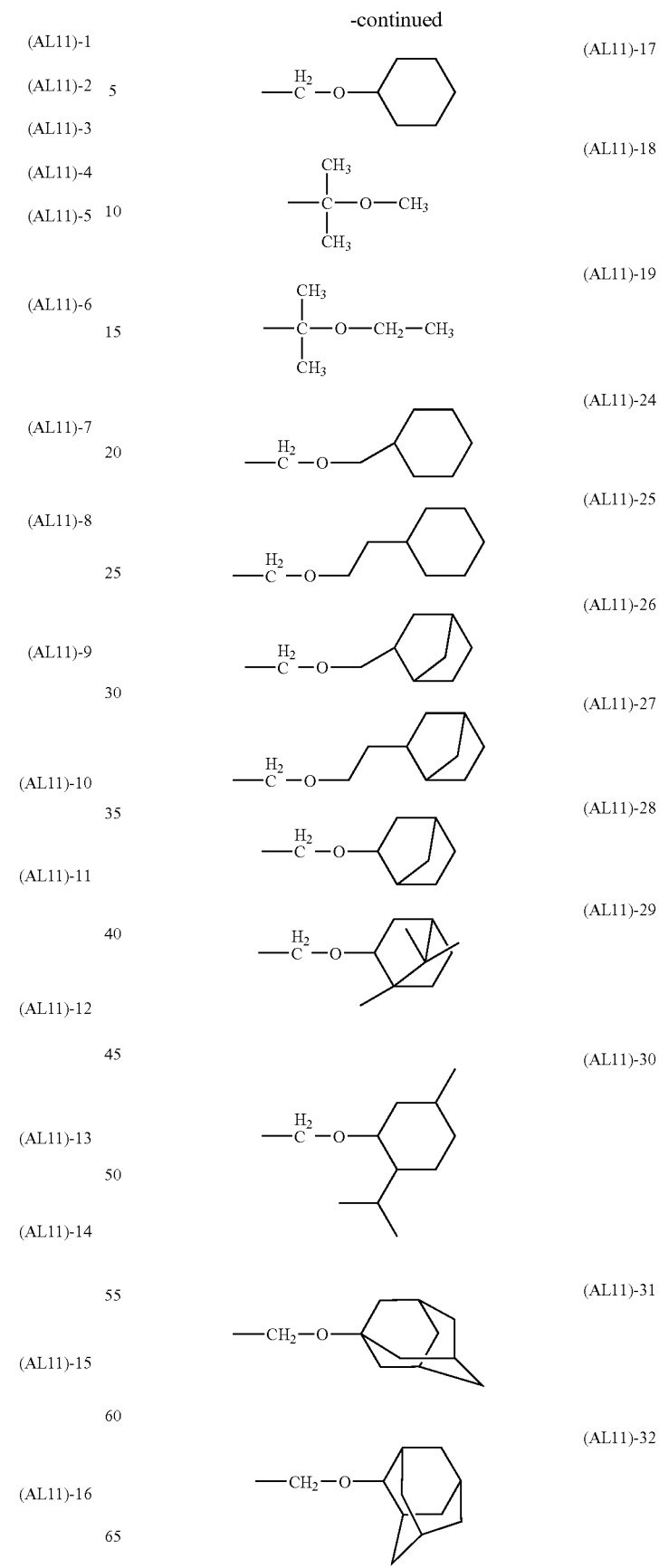

(AL11)-33
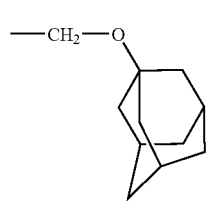
Examples of the tertiary alkyl group shown in the above-mentioned formula (AL12) may include: tert-butyl group, triethyl carbyl group, 1-ethyl norbornyl group, 1-methyl cyclohexyl group, 1-ethyl cyclopentyl group, tert-amyl group or the like, and those represented by the following general formulae (AL12)-1 to (AL12)-16.
(AL12)-1
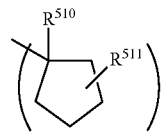
(AL12)-2
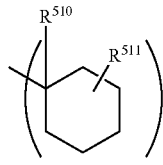
(AL12)-3
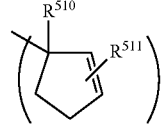
(AL12)-4
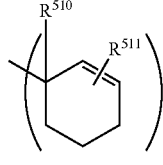
(AL12)-5
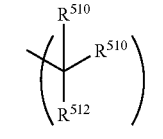
(AL12)-6
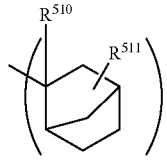
(AL12)-7
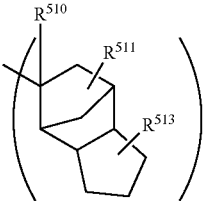
(AL12)-8
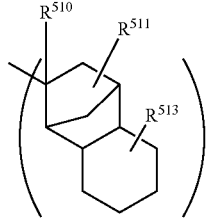
(AL12)-9
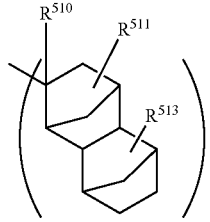
(AL12)-10
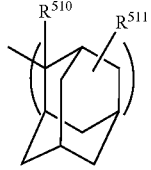
(AL12)-11
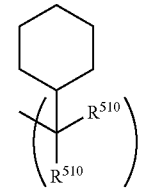
(AL12)-12
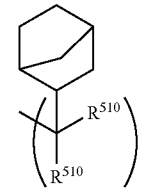
(AL12)-13
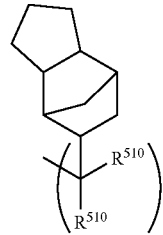
(AL12)-14
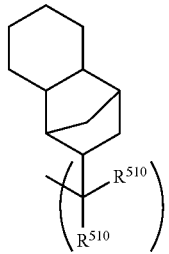

-continued (AL12)-15
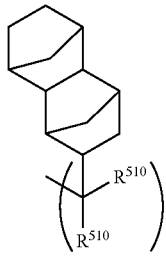

(AL12)-16
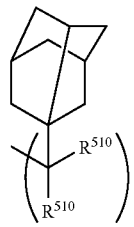

In the above-mentioned formula, $R^{510}$ may be the same or different, and represents a linear, branched or cyclic alkyl group having 1–8 carbon atoms, an aryl group or aralkyl group having 6–20 carbon atoms. $R^{511}$ and $R^{513}$ do not exist, or represent a linear, branched or cyclic alkyl group having 1–20 carbon atoms. $R^{512}$ represents an aryl group or aralkyl group having 6–20 carbon atoms.

Furthermore as shown in (AL12)-19 and (AL12)-20, a bridge may be formed in the molecule or between the molecules of the polymer, including $R^{514}$ which is an alkylene group or arylene group with bivalent or more. $R^{510}$ in the formula (AL12)-19 and (AL12)-20 may be the same as mentioned above, and $R^{514}$ may represent a linear, branched or cyclic alkylene group or arylene group having 1–20 carbon atoms, and may contain hetero atoms such as an oxygen atom, a sulfur atom, a nitrogen atom and the like. b6 is an integer of 1–3.

(AL12)-19
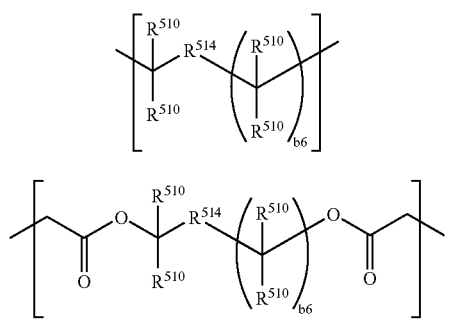

(AL12)-20

Furthermore, $R^{510}$, $R^{511}$, $R^{512}$, and $R^{513}$ may have hetero atoms, such as oxygen, nitrogen, sulfur or the like. Illustratively, they may be shown by the following (AL13)-1 to (AL13)-7.

—(CH$_2$)$_4$—OH (AL13)-1

—(CH$_2$)$_2$O(CH$_2$)$_3$CH$_3$ (AL13)-2

-continued

 (AL13)-3

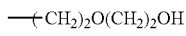 (AL13)-4

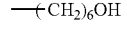 (AL13)-5

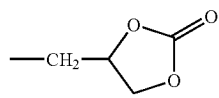 (AL13)-6

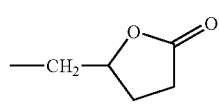 (AL13)-7

The polymeric material of the present invention indispensably contains the repeating unit represented by the general formula (1c), and it is obtained by copolymerizing the repeating unit represented by the general formula (1c) and one or more of the repeating units represented by the general formulae (1a), (2a) and (3b). Furthermore, the repeating unit represented by the general formula (1d) can also be copolymerized therewith. Furthermore, the repeating unit which has an adhesion group other than the repeating units represented by a general formulae (1a), (2a), (1c), (3b), and (1d) can also be copolymerized therewith. Illustratively, the repeating unit which has an adhesion group can be the repeating unit e wherein the monomers (1e) specifically illustrated below are polymerized.

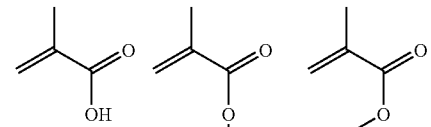

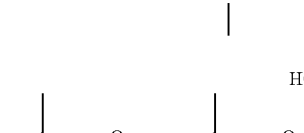

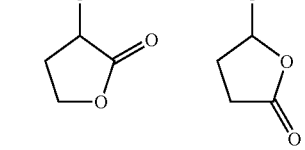

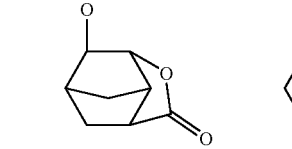

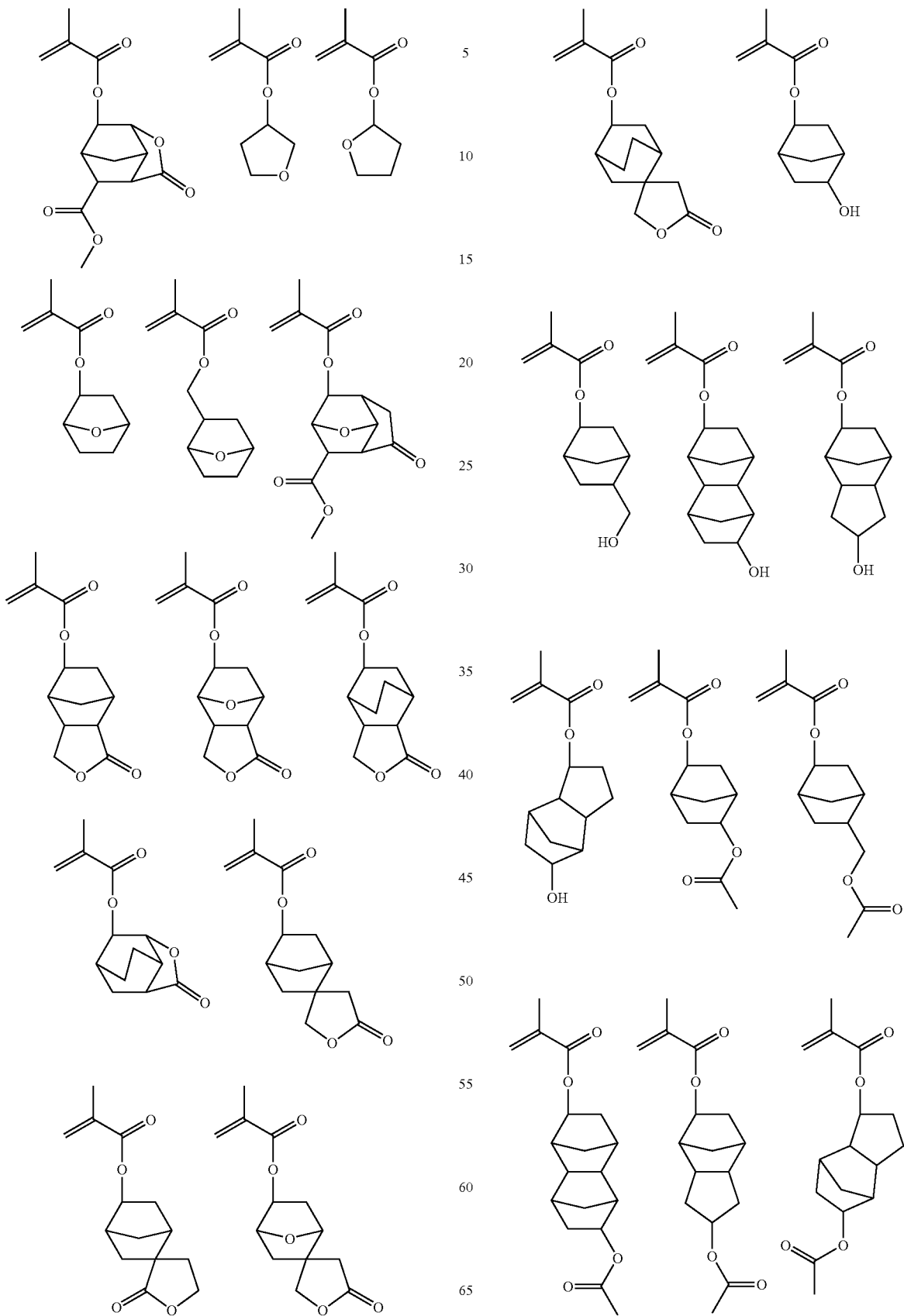

-continued
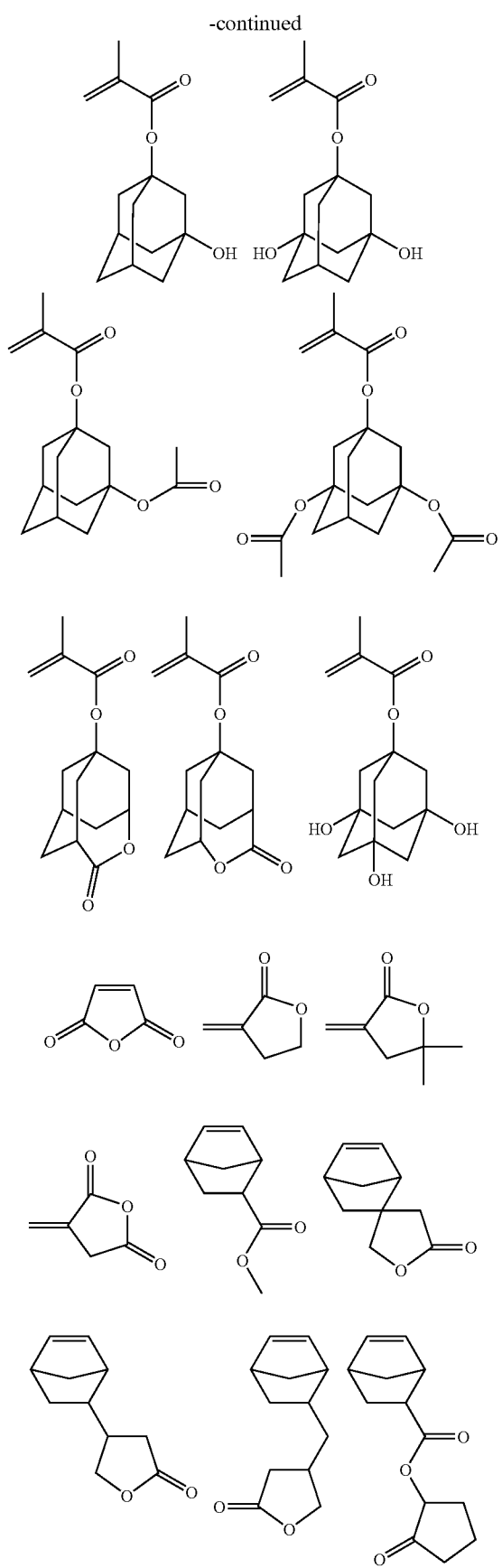
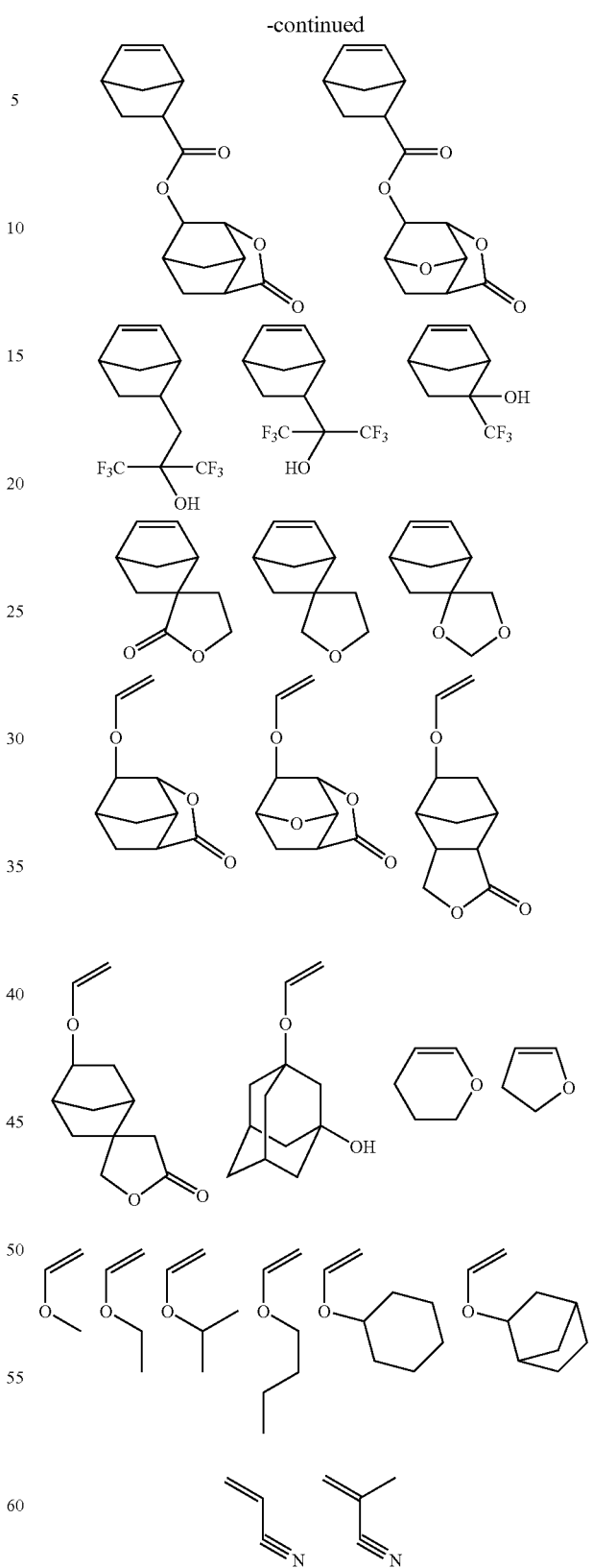
In the general formulae (1a), (2a), (1c), (3b), and (1d), a ratio of the repeating units a1, a2, c, b3 and d is the value such that $0 \leq a1 \leq 0.8$, $0 \leq a2 \leq 0.8$, $0 \leq b3 \leq 0.8$, $0.1 \leq a1+a2+$ b3≦0.8, 0<c≦0.9, 0≦d≦0.8, preferably 0≦a1≦0.7, 0≦a2≦0.7, 0≦b3≦0.7, 0.15≦a1+a2+b3≦0.7, 0.1≦c≦0.9, and 0≦d≦0.7.

Furthermore, when the monomer (1e) is copolymerized, the ratio of the repeating unit e is the value such that 0≦e/(a1+a2+c+b3+d+e)≦0.8, preferably 0≦e/(a1+a2+c+b3+d+e)≦0.7.

The polymer of the present invention each needs to have a weight average molecular weight (a measuring method is as mentioned below) of 1,000–500,000, preferably 2,000–30,000. If the weight average molecular weight is too small, a heat resistance of the resist composition will be degraded. If it is too large, an alkali solubility will be lowered, and it will become easy to cause a footing profile after pattern formation.

Furthermore, in the polymer of the present invention, when a molecular weight distribution (Mw/Mn) is large, there is a possibility that impurities may be observed on a pattern, or a shape of a pattern may be degraded after exposure, since there exist both of the polymer with low molecular weight and the polymer with high molecular weight. So, if the pattern rule becomes finer, the influence by a molecular weight or a dispersion of a molecular weight easily gets larger. Accordingly, in order to obtain the resist composition used suitably for a micropattern size, it is desirable to use a multi-component copolymer with a narrow molecular weight distribution as 1.0–2.0, preferably 1.0–1.5.

Moreover, it is also possible to blend two or more polymers having a different composition ratio, a different molecular weight distribution, or a different molecular weight.

In order to synthesize these polymers, there is a method of adding a radical initiator to a monomer which has a unsaturated bond for obtaining the repeating units a1, a2, c, b3 and d, and the monomer represented by the repeating unit e in organic solvent, to perform heating polymerization, and thereby, a polymer can be obtained. Examples of the organic solvent used at the time of polymerization may include: toluene, benzene, tetrahydrofuran, diethyl ether, dioxane, and the like. Examples of the polymerization initiator may include: 2,2'-azobisisobutyronitril (AIBN), 2,2'-azo bis(2,4-dimethyl valeronitrile), dimethyl 2,2-azo bis(2-methyl propionate), benzoyl peroxide, lauroyl peroxide, and the like. Polymerization can be conducted preferably by heating at 50° C. to 80° C. The reaction time may be 2 to 100 hours, preferably 5–20 hours. The acid labile group may be used as those introduced into the monomer, or the acid labile group may be released by an acid catalyst once and then protected or partially protected.

The positive-resist composition of the present invention may contain, organic solvent, and the compound which perceives a high energy beam and generates an acid (acid generator), and if necessary a dissolution inhibitor, a basic compound, a surfactant, and other components.

Organic solvents used for the resist composition of the present invention, especially chemically amplified positive-resist composition can be any organic solvents in which a base resin, an acid generator, and other additives can be dissolved. Examples of such an organic solvent may include: ketones such as cyclohexanone, methyl-2-n-amyl ketone and the like; alcohols such as 3-methoxy butanol, 3-methyl-3-methoxy butanol, 1-methoxy-2-propanol, 1-ethoxy-2-propanol and the like; ethers such as propylene glycol monomethyl ether, ethylene glycol monomethyl ether, propyleneglycol monomethyl ether, ethylene glycol monoethyl ether, propyleneglycol dimethyl ether, diethyleneglycol dimethyl ether and the like; esters such as propyleneglycolmonomethylether acetate, propyleneglycol monoethylether acetate, ethyl lactate, ethyl pyruvate, butyl acetate, methyl 3-methoxypropionate, ethyl 3-ethoxypropionate, tert-butyl acetate, tert-butyl propionate, propyleneglycol monotertbutylether acetate and the like; lactones such as γ-butyrolactone; and the like. They can be used alone or in admixture of two or more of them. However, they are not limitative. Among the above-mentioned organic solvents, diethyleneglycoldimethylether, 1-ethoxy-2-propanol, propyleneglycolmonomethylether acetate, and a mixed solvent thereof in which an acid generator in the resist component is dissolved best are preferably used.

The amount of the organic solvent to be used is preferably 200 to 10,000 parts (by weight), especially 400 to 800 parts to 100 parts of the base resin.

Examples of the acid generator used in the present invention are as follow:
i) an onium salt represented by the following general formula (P1a-1), (P1a-2) or (P1b)
ii) a diazomethane derivative represented by the following general formula (P2),
iii) a glyoxime derivative represented by the following general formula (P3),
iv) a bis sulfone derivative represented by the following general formula (P4),
v) a sulfonate of a N-hydroxy imide compound represented by the following general formula (P5),
vi) a β-keto sulfonic-acid derivative,
vii) a disulfone derivative,
viii) a nitro benzyl sulfonate derivative,
ix) a sulfonate derivative, or the like.

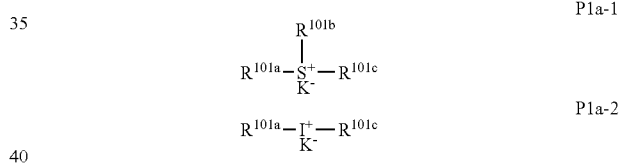

(In the formulae, $R^{101a}$, $R^{101b}$, and $R^{101c}$ independently represent a linear, branched or cyclic alkyl group, alkenyl group, oxoalkyl group or oxoalkenyl group each having 1–12 carbon atoms, an aryl group having 6–20 carbon atoms, or an aralkyl group or an aryl oxoalkyl group having 7–12 carbon atoms. Some or all of hydrogen atoms of these groups may be substituted with an alkoxy group or the like. $R^{101b}$ and $R^{101c}$ may constitute a ring. In the case that they constitute a ring, $R^{101b}$ and $R^{101c}$ represent an alkylene group having 1–6 carbon atoms respectively. $K^-$ represents a non-nucleophilic counter ion.) The above-mentioned $R^{101a}$, $R^{101b}$ and $R^{101c}$ may be the same or different. Illustrative examples thereof as an alkyl group may include: a methyl group, an ethyl group, a propyl group, an isopropyl group, n-butyl group, sec-butyl group, tert-butyl group, a pentyl group, a hexyl group, a heptyl group, an octyl group, a cyclopentyl group, a cyclohexyl group, a cycloheptyl group, a cyclopropyl methyl group, 4-methyl cyclohexyl group, a cyclohexyl methyl group, a norbornyl group, an adamantyl group, or the like. Illustrative examples of an alkenyl group may include: a vinyl group, an allyl group, a propenyl group, a butenyl group, a hexenyl group, a cyclohexenyl group, or the like. Examples of an oxoalkyl group may include: 2-oxocyclopentyl group, 2-oxocyclohexyl group, 2-oxopropyl group, 2-cyclopentyl-2-oxoethyl group, 2-cyclohexyl-2-oxoethyl group, 2-(4-methylcyclohexyl)-2- oxoethyl group, and the like. Examples of the oxoalkenyl group may include: 2-oxo-4-cyclohexenyl group, 2-oxo-4-propenyl group and the like. Examples of an aryl group may include: a phenyl group, a naphthyl group, an alkoxy phenyl group such as p-methoxyphenyl group, m-methoxyphenyl group, o-methoxyphenyl group, an ethoxyphenyl group, p-tert-butoxyphenyl group, m-tert-butoxy phenyl group and the like, an alkyl phenyl group such as 2-methylphenyl group, 3-methylphenyl group, 4-methylphenyl group, an ethylphenyl group, 4-tert-butylphenyl group, 4-butylphenyl group, a dimethyl phenyl group and the like, an alkyl naphthyl group such as a methylnaphthyl group, an ethyl naphthyl group and the like, an alkoxy naphthyl group such as a methoxy naphthyl group, an ethoxy naphthyl group and the like, a dialkyl naphthyl group such as a dimethyl naphthyl group, a diethyl naphthyl group and the like, and a dialkoxy naphthyl group such as a dimethoxy naphthyl group, a diethoxy naphthyl group and the like. Examples of the aralkyl group may include a benzyl group, a phenylethyl group, a phenethyl group and the like. Examples of an aryl oxoalkyl group may include: 2-aryl-2-oxoethyl group such as 2-phenyl-2-oxoethyl group, 2-(1-naphthyl)-2-oxoethyl group, and 2-(2-naphthyl)-2-oxoethyl group, and the like. Examples of an non-nucleophilic counter ion as K$^-$ may include: a halide ion such as a chloride ion, a bromide ion or the like, a fluoro alkyl sulfonate such as triflate, 1,1,1-trifluoro ethanesulfonate, nonafluoro butane sulfonate and the like, an aryl sulfonate such as tosylate, benzene sulfonate, 4-fluorobenzene sulfonate, 1,2,3,4,5-pentafluoro benzene sulfonate and the like, and an alkyl sulfonate such as mesylate, butane sulfonate and the like.

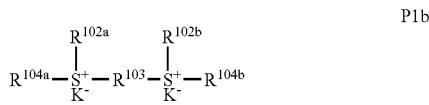

(In the formula, $R^{102a}$ and $R^{102b}$ each represent a linear, branched or cyclic alkyl group having 1–8 carbon atoms. $R^{103}$ represents a linear, branched or cyclic alkylene group having 1–10 carbon atoms. $R^{104a}$ and $R^{104b}$ each represent a 2-oxoalkyl group having 3–7 carbon atoms. K$^-$ represents an non-nucleophilic counter ion.)

Illustrative examples of the above-mentioned $R^{102a}$ and $R^{102b}$ may include: a methyl group, an ethyl group, a propyl group, an isopropyl group, n-butyl group, sec-butyl group, tert-butyl group, a pentyl group, a hexyl group, a heptyl group, an octyl group, a cyclopentyl group, a cyclohexyl group, a cyclopropylmethyl group, 4-methylcyclohexyl group, a cyclohexyl methyl group and the like. Examples of $R^{103}$ may include: a methylene group, an ethylene group, a propylene group, a butylene group, a pentylene group, a hexylene group, a heptylene group, an octylene group, a nonylene group, 1,4-cyclohexylene group, 1,2-cyclohexylene group, 1,3-cyclopentylene group, 1,4-cyclooctylene group, 1,4-cyclohexane dimethylene group and the like. Examples of $R^{104a}$ and $R^{104b}$ may include: 2-oxopropyl group, 2-oxocyclopentyl group, 2-oxocyclohexyl group, 2-oxocycloheptyl group and the like. As K$^-$, the same as mentioned in the formulae (P1a-1) and (P1a-2) can be exemplified.

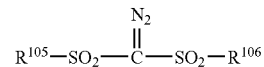

(In the fromula, $R^{105}$ and $R^{106}$ represent a linear, branched or cyclic alkyl group or alkyl-halide group having 1–12 carbon atoms, an aryl group or aryl-halide group having 6–20 carbon atoms, or an aralkyl group having 7–12 carbon atoms.)

Examples of the alkyl group as $R^{105}$ and $R^{106}$ may include: a methyl group, an ethyl group, a propyl group, an isopropyl group, n-butyl group, sec-butyl group, tert-butyl group, a pentyl group, a hexyl group, a heptyl group, an octyl group, an amyl group, a cyclopentyl group, a cyclohexyl group, a cycloheptyl group, a norbornyl group, an adamantyl group and the like. Examples of the alkyl-halide group as $R^{105}$ and $R^{106}$ may include: trifluoromethyl group, 1,1,1-trifluoroethyl group, 1,1,1-trichloroethyl group, a nonafluoro butyl group and the like. Examples of the aryl group as $R^{105}$ and $R^{106}$ may include: a phenyl group, an alkoxyphenyl group such as p-methoxyphenyl group, m-methoxyphenyl group, o-methoxyphenyl group, an ethoxyphenyl group, p-tert-butoxyphenyl group, m-tert-butoxyphenyl group and the like, and an alkylphenyl group such as 2-methylphenyl group, 3-methylphenyl group, 4-methylphenyl group, an ethylphenyl group, 4-tert-butylphenyl group, 4-butylphenyl group, a dimethylphenyl group and the like. Examples of the aryl-halide group of $R^{105}$ and $R^{106}$ may include: a fluorophenyl group, a chlorophenyl group, 1,2,3,4,5-pentafluoro phenyl group and the like. Examples of the aralkyl group of $R^{105}$ and $R^{106}$ may include: a benzyl group, a phenethyl group, and the like.

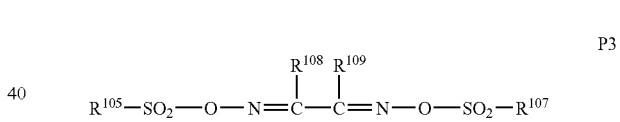

(In the formula, $R^{107}$, $R^{108}$ and $R^{109}$ represents a linear, branched or cyclic alkyl group or halogenated alkyl group having 1 to 12 carbon atoms, an aryl group or a halogenated aryl group having 6 to 20 carbon atoms, or an aralkyl group having 7 to 12 carbon atoms. $R^{108}$ and $R^{109}$ may bond to each other to form a cyclic structure. When they form a cyclic structure, $R^{108}$ and $R^{109}$ each represent a linear or branched alkylene group having 1 to 6 carbon atoms. $R^{105}$ represents the same as that of the formula P2.)

Examples of the alkyl group, the halogenated alkyl group, the aryl group, the halogenated aryl group, and the aralkyl group as $R^{107}$, $R^{108}$ and $R^{109}$ may be the same as exemplified for $R^{105}$ and $R^{106}$. In addition, as an alkylene group for $R^{108}$ and $R^{109}$, a methylene group, an ethylene group, a propylene group, a butylene group, a hexylene group and the like may be exemplified.

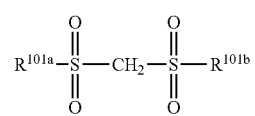

(In the formula, $R^{101a}$ and $R^{101b}$ are the same as explained above.)

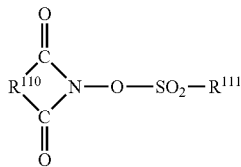

P5

(In the formula, $R^{110}$ represents an arylene group having 6–10 carbon atoms, an alkylene group having 1–6 carbon atoms or an alkenylene group having 2–6 carbon atoms. Some or all of hydrogen atoms of these groups may be further substituted with a linear or branched alkyl group or an alkoxy group having 1–4 carbon atoms, a nitro group, an acetyl group, or a phenyl group. $R^{111}$ represents a linear, branched or substituted alkyl group, alkenyl group or alkoxy alkyl group having 1–8 carbon atoms, a phenyl group or a naphthyl group. Some or all of hydrogen atoms of these groups may be substituted with an alkyl group or an alkoxy group having 1–4 carbon atoms; a phenyl group which may be substituted with an alkyl group or an alkoxy group having 1–4 carbon atoms, a nitro group or an acetyl group; a hetero aromatic group having 3–5 carbon atoms; or a chlorine atom or a fluorine atom.)

Examples of the arylene group as $R^{110}$ may include: 1,2-phenylene group, 1,8-naphtylene group and the like. Examples of the alkylene group may include: a methylene group, an ethylene group, a trimethylene group, a tetramethylene group, a phenylethylene group, a norbornane 2,3-di-yl group, and the like. Examples of the alkenylene group may include: 1,2-vinylene group, 1-phenyl-1,2-vinylene group, 5-norbornene-2,3-di-yl group and the like. Examples of the alkyl group as $R^{111}$ may be the same as exemplified for $R^{101a}$–$R^{101c}$. Examples of the alkenyl group as $R^{111}$ may include: a vinyl group, 1-propenyl group, an allyl group, 1-butenyl group, 3-butenyl group, an isoprenyl group, 1-pentenyl group, 3-pentenyl group, 4-pentenyl group, a dimethyl allyl group, 1-hexenyl group, 3-hexenyl group, 5-hexenyl group, 1-heptenyl group, 3-heptenyl group, 6-heptenyl group, 7-octenyl group and the like. Examples of the alkoxy alkyl group may include: a methoxy methyl group, an ethoxy methyl group, a propoxy methyl group, a butoxy methyl group, a pentyloxy methyl group, a hexyloxy methyl group, a heptyloxy methyl group, a methoxy ethyl group, an ethoxy ethyl group, a propoxy ethyl group, a butoxy ethyl group, pentyloxy ethyl group, a hexyloxy ethyl group, a methoxy propyl group, ethoxy propyl group, a propoxy propyl group, a butoxy propyl group, a methoxy butyl group, an ethoxy butyl group, a propoxy butyl group, a methoxy pentyl group, an ethoxy pentyl group, a methoxy hexyl group, a methoxy heptyl group and the like.

In addition, examples of the alkyl group having 1–4 carbon atoms with which the hydrogen atoms may be further substituted may include: a methyl group, an ethyl group, a propyl group, an isopropyl group, n-butyl group, an isobutyl group, a tert-butyl group and the like. Examples of the alkoxy group having 1–4 carbon atoms may include: a methoxy group, an ethoxy group, a propoxy group, an isopropoxy group, n-butoxy group, an isobutoxy group, a tert-butoxy group and the like. Examples of the phenyl group which may be substituted with an alkyl group and an alkoxy group having 1–4 carbon atoms, a nitro group or an acetyl group may include: a phenyl group, a tolyl group, p-tert-butoxy phenyl group, p-acetyl phenyl group, p-nitrophenyl group and the like. Examples of a hetero aromatic group having 3–5 carbon atoms may include: a pyridyl group, a furyl group and the like.

Illustrative examples of an acid generator follow. Examples of the onium salt may include: diphenyl iodonium trifluoromethane sulfonate, (p-tert-butoxyphenyl)phenyl iodonium trifluoromethane sulfonate, diphenyliodonium p-toluenesulfonate, (p-tert-butoxyphenyl)phenyliodionium p-toluenesulfonate, triphenylsulfonium trifluoromethane sulfonate, (p-tert-butoxy phenyl)diphenyl sulfonium trifluoromethane sulfonate, bis(p-tert-butoxy phenyl)phenyl sulfonium trifluoromethane sulfonate, tris(p-tert-butoxy phenyl) sulfonium trifluoromethane sulfonate, triphenyl sulfonium p-toluenesulfonate, (p-tert-butoxy phenyl)diphenyl sulfonium p-toluenesulfonate, bis(p-tert-butoxy phenyl)phenyl sulfonium p-toluenesulfonate, tris(p-tert-butoxy phenyl)sulfonium p-toluenesulfonate, triphenyl sulfonium nonafluoro butane sulfonate, triphenyl sulfonium butane sulfonate, trimethyl sulfonium trifluoromethane sulfonate, trimethyl sulfonium p-toluenesulfonate, cyclohexyl methyl (2-oxocyclohexyl)sulfonium trifluoromethane sulfonate, cyclohexyl methyl (2-oxo cyclohexyl)sulfonium p-toluenesulfonate, dimethyl phenyl sulfonium trifluoromethane sulfonate, dimethyl phenyl sulfonium p-toluenesulfonate, dicyclohexyl phenyl sulfonium trifluoromethane sulfonate, dicyclohexyl phenyl sulfonium p-toluenesulfonate, trinaphthylsulfonium trifluoromethane sulfonate, (2-norbonyl)methyl (2-oxocyclohexyl)sulfonium trifluoromethane sulfonate, ethylene bis [methyl(2-oxocyclopentyl)sulfonium trifluoromethane sulfonate], 1,2'-naphthyl carbonyl methyltetrahydro thiophenium triflate, and the like.

Examples of the diazomethane derivative may include: bis(benzene sulfonyl)diazomethane, bis(p-toluene sulfonyl) diazomethane, bis(xylene sulfonyl)diazomethane, bis(cyclohexyl sulfonyl)diazomethane, bis(cyclopentyl sulfonyl)diazomethane, bis(n-butylsulfonyl)diazomethane, bis(isobutyl sulfonyl)diazomethane, bis(sec-butylsulfonyl)diazomethane, bis(n-propylsulfonyl)diazomethane, bis(isopropyl sulfonyl)diazomethane, bis(tert-butyl-sulfonyl)diazomethane, bis(n-amylsulfonyl)diazomethane, bis (isoamylsulfonyl)diazomethane, bis(sec-amylsulfonyl) diazomethane, bis(tert-amylsulfonyl)diazomethane, 1-cyclohexylsulfonyl-1-(tert-butylsulfonyl)diazomethane, 1-cyclohexyl sulfonyl-1-(tert-amyl sulfonyl)diazomethane, 1-tert-amyl sulfonyl-1-(tert-butylsulfonyl)diazomethane and the like.

Examples of the glyoxime derivative may include: bis-O-(p-toluene sulfonyl)-α-dimethylglyoxime, bis-O-(p-toluene sulfonyl)-α-diphenyl glyoxime, bis-O-(p-toluene sulfonyl)-α-dicyclohexyl glyoxime, bis-O-(p-toluene sulfonyl)-2,3-pentanedione glyoxime, bis-O-(p-toluene sulfonyl)-2-methyl-3,4-pentanedione glyoxime, bis-O-(n-butane sulfonyl)-α-dimethylglyoxime, bis-O-(n-butane sulfonyl)-α-diphenyl glyoxime, bis-O-(n-butane sulfonyl)-α-dicyclohexyl glyoxime, bis-O-(n-butane sulfonyl)-2,3-pentanedione glyoxime, bis-O-(n-butane sulfonyl)-2-methyl-3,4-pentanedione glyoxime, bis-O-(methane sulfonyl)-α-dimethylglyoxime, bis-O-(trifluoromethane sulfonyl)-α-dimethylglyoxime, bis-O-(1,1,1-trifluoro ethane sulfonyl)-α-dimethylglyoxime, bis-O-(tert-butane sulfonyl)-α-dimethylglyoxime, bis-O-(perfluoro octane sulfonyl)-α-dimethylglyoxime, bis-O-(cyclohexane sulfonyl)-α-dimethylglyoxime, bis-O-(benzene sulfonyl)-α-dimethylglyoxime, bis-O-(p-fluorobenzene sulfonyl)-α-dimethylglyoxime, bis-O-(p-tert-butylbenzene sulfonyl)-α- dimethylglyoxime, bis-O-(xylene sulfonyl)-α-dimethylglyoxime, bis-O-(camphor sulfonyl)-α-dimethylglyoxime and the like.

Examples of the bissulfone derivative may include: bis naphthyl sulfonyl methane, bistrifluoro methyl sulfonyl methane, bis methyl sulfonyl methane, bis ethyl sulfonyl methane, bis propyl sulfonyl methane, bis isopropyl sulfonyl methane, bis-p-toluene sulfonyl methane, bis benzene sulfonyl methane and the like.

Examples of the β-ketosulfone derivative may include: 2-cyclohexyl carbonyl-2-(p-toluene sulfonyl)propane, 2-isopropyl carbonyl-2-(p-toluene sulfonyl)propane and the like.

Examples of the disulfone derivative may include: diphenyl disulfone derivative, a diyclohexyl disulfone derivative and the like.

Examples of the nitro benzyl sulfonate derivative may include: 2,6-dinitro benzyl p-toluenesulfonate, 2,4-dinitro benzyl p-toluenesulfonate, and the like.

Examples of the sulfonate derivative may include: 1,2,3-tris(methane sulfonyloxy)benzene, 1,2,3-tris(trifluoromethane sulfonyloxy)benzene, 1,2,3-tris(p-toluene sulfonyloxy)benzene, and the like.

Examples of the sulfonate derivative of N-hydroxy imide compound may include: N-hydroxy succinimide methane sulfonate, N-hydroxy succinimide trifluoromethane sulfonate, N-hydroxy succinimide ethane sulfonate, N-hydroxy succinimide 1-propane sulfonate, N-hydroxy succinimide 2-propane sulfonate, N-hydroxy succinimide 1-pentane sulfonate, N-hydroxy succinimide 1-octane sulfonate, N-hydroxy succinimide p-toluenesulfonic-acid ester, N-hydroxy succinimide p-methoxybenzene sulfonate, N-hydroxy succinimide 2-chloroethane sulfonate, N-hydroxy succinimide benzenesulfonic-acid ester, N-hydroxy succinimide-2,4,6-trimethyl benzene sulfonate, N-hydroxy succinimide 1-naphthalene sulfonate, N-hydroxy succinimide 2-naphthalene sulfonate, N-hydroxy-2-phenyl succinimide methane sulfonate, N-hydroxy maleimide methane sulfonate, N-hydroxy maleimide ethane sulfonate, N-hydroxy-2-phenyl maleimide methane sulfonate, N-hydroxy glutarimide methane sulfonate, N-hydroxy glutarimide benzenesulfonic-acid ester, N-hydroxy phthalimide methane sulfonate, N-hydroxy phthalimide benzenesulfonic-acid ester, N-hydroxy phthalimide trifluoromethane sulfonate, N-hydroxy phthalimide p-toluenesulfonic-acid ester, N-hydroxy naphthalimide methane sulfonate, N-hydroxy naphthalimide benzenesulfonic-acid ester, N-hydroxy-5-norbornene-2,3-dicarboxyimido methane sulfonate, N-hydroxy-5-norbornene-2,3-dicarboxyimido trifluoromethane sulfonate, N-hydroxy-5-norbornene-2,3-dicarboxyimido p-toluenesulfonate and the like.

Preferable examples thereof may include: the onium salt such as triphenyl sulfonium trifluoromethane sulfonate, (p-tert-butoxy phenyl)diphenyl sulfonium trifluoromethane sulfonate, tris(p-tert-butoxy phenyl)sulfonium trifluoromethane sulfonate, triphenyl sulfonium p-toluenesulfonate, (p-tert-butoxy phenyl)diphenyl sulfonium p-toluenesulfonate, tris(p-tert-butoxy phenyl)sulfonium p-toluenesulfonate, trinaphthylsulfonium trifluoromethane sulfonate, cyclohexyl methyl (2-oxocyclohexyl)sulfonium trifluoromethane sulfonate, (2-norbornyl)methyl (2-oxocyclohexyl)sulfonium trifluoromethane sulfonate, 1,2'-naphthyl carbonylmethyl tetrahydrothiophenium triflate, and the like;

the diazomethane derivative such as bis(benzene sulfonyl)diazomethane, bis(p-toluene sulfonyl)diazomethane, bis(cyclohexyl sulfonyl)diazomethane, bis(n-butylsulfonyl) diazomethane, bis(isobutyl sulfonyl)diazomethane, bis(sec-butylsulfonyl) diazomethane, bis(n-propyl sulfonyl) diazomethane, bis(isopropyl sulfonyl)diazomethane, bis(tert-butylsulfonyl)diazomethane and the like;

the glyoxime derivative such as bis-O-(p-toluene sulfonyl)-α-dimethylglyoxime and bis-O-(n-butane sulfonyl)-α-dimethylglyoxime and the like;

the bissulfone derivative such as bisnaphthyl sulfonyl methane;

a sulfonate derivative of N-hydroxyimide compound such as N-hydroxy succinimide methane sulfonate, N-hydroxy succinimide trifluoromethane sulfonate, N-hydroxy succinimide 1-propane sulfonate, N-hydroxy succinimide 2-propane sulfonate, N-hydroxy succinimide 1-pentane sulfonate, N-hydroxy succinimide p-toluene sulfonate, N-hydroxy naphthalimide methane sulfonate and N-hydroxy naphthalimide benzene sulfonate.

The above-mentioned acid generator may be used alone or in admixture of two or more kinds of them. The onium salt is excellent in an effect of achieving a straight wall profile. The diazomethane derivative and the glyoxime derivative are excellent in an effect of reducing standing wave. Therefore, if both of them are combined, minute control of profile can be conducted.

An amount of the acid generator to be added is preferably 0.1 to 50 parts (parts by weight, hereinafter represents the same meaning), more preferably 0.5 to 40 parts to 100 parts of a base polymer. If it is fewer than 0.1 parts, an amount of acid generated in exposure is few, and sensitivity and resolution is inferior in some cases. If it exceeds 50 parts, transmittance of the resist is lowered, and resolution is inferior in some cases.

The dissolution inhibitor (dissolution control agent) blended in the positive-resist composition of the present invention, especially chemically amplified positive-resist composition may be a compound which has an average molecular weight of 100 to 1,000, preferably 150 to 800. And the compound may have two or more phenolic hydroxyl group in a molecular in which 0 to 100 mole % on average of hydrogens of the phenolic hydroxyl groups are substituted with an acid labile group. Or the compound may have carboxyl groups in a molecular in which 50 to 100 mole % on average of hydrogens of the carboxyl groups are substituted with an acid labile group.

A substitution ratio of hydrogens of phenolic hydroxyl groups substituted with acid labile group is 0 mole % or more, preferably 30 mole % or more on average to total phenolic hydroxyl group. The upper limit thereof is 100 mole %, preferably 80 mole %. A substitution ratio of hydrogen of carboxyl groups substituted with acid labile group is 50 mole % or more, preferably 70 mole % or more on average to total carboxyl group. The upper limit thereof is 100 mole %.

In this case, the compound having two or more phenolic hydroxyl groups or the compound having carboxyl groups may be those represented by the following formula (D1) to (D14).

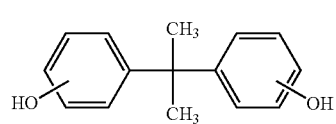

D1

-continued

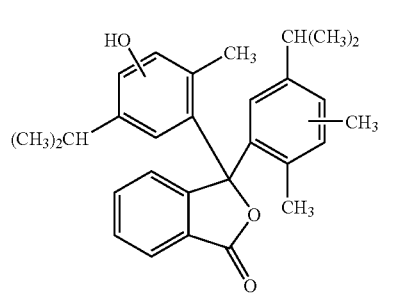
D2

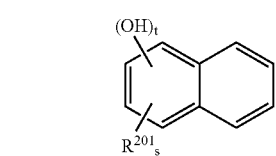
D3

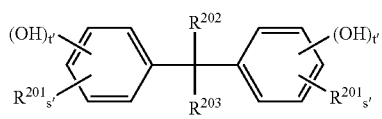
D4

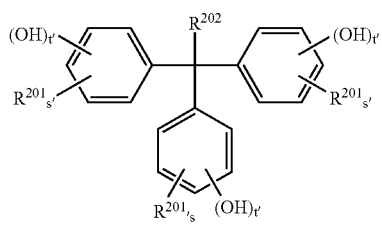
D5

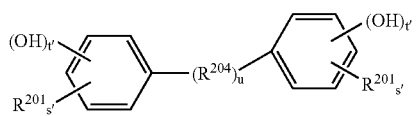
D6

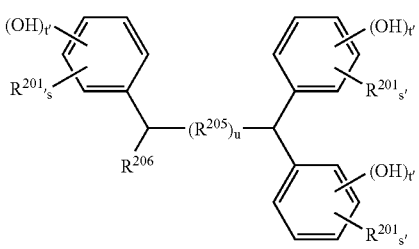
D7

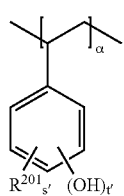
D8

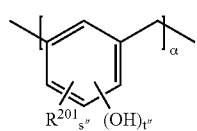
D9

-continued

D10

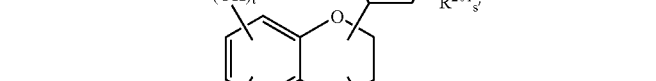
D11

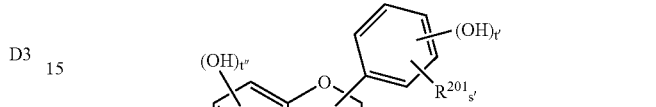
D12

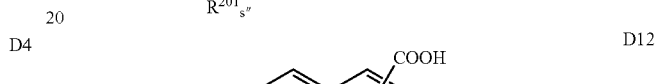
D13

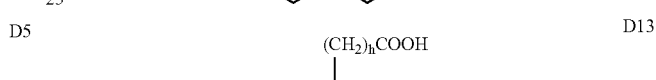
D14

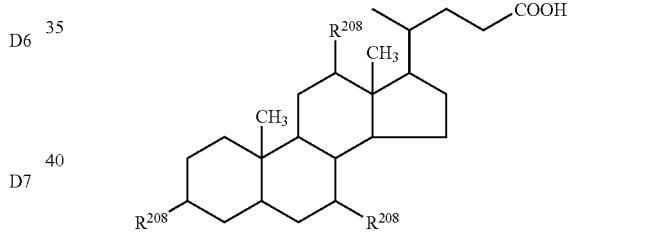

In the formulae, $R^{201}$ and $R^{202}$ each represents a hydrogen or a linear or branched alkyl group or alkenyl group having 1–8 carbon atoms. $R^{203}$ represents a hydrogen, a linear or branched alkyl group or alkenyl group, or —$(R^{207})_h$COOH. $R^{204}$ represents —$(CH_2)_i$—(i=2 to 10), an arylene group having 6–10 carbon atoms, a carbonyl group, a sulfonyl group, an oxygen atom or a sulfur atom. $R^{205}$ represents an alkylene group having 1–10 carbon atoms, an arylene group having 6–10 carbon atoms, a carbonyl group, a sulfonyl group, an oxygen atom or a sulfur atom. $R^{206}$ represents a hydrogen atom, a linear or branched alkyl group or alkenyl group having 1–8 carbon atoms, or a phenyl group or a naphthyl group which are substituted with a hydroxyl group respectively. $R^{207}$ represents a linear or branched alkylene group having 1–10 carbon atoms. $R^{208}$ represents a hydrogen atom or a hydroxyl group. j is an integer of 0 to 5. u and h are 0 or 1. s, t, s',t',s'' and t'' are the number satisfying the formula: s+t=8, s'+t'=5, s''+t''=4, such that at least one hydroxyl group is contained in each of phenyl skeletons. α is the number such that a molecular weight of the compound represented by (D8), (D9) may be 100 to 1000.

The weight average molecular weight of the above-mentioned compound is 100 to 1000, preferably 150 to 800. The amount of the dissolution inhibitor to be blended is 0 to 50 parts by weight, preferably 5 to 50 parts by weight, more preferably 10 to 30 parts by weight, to parts by weight of a base resin. The dissolution inhibitor may be used alone or in admixture of two or more kinds of them. If the amount to be blended is too few, resolution cannot be improved in some cases. If it is too much, a film loss in a pattern may be caused, and resolution tends to be lowered.

Furthermore, the basic compound can be blended in the positive resist composition of the present invention, especially the chemically amplified positive-resist composition.

Suitable compound as the basic compound is a compound which can control diffusion rate of the acid generated by acid generator when it is diffused in the resist film. If the basic compound is blended, the diffusion rate of the acid in the resist film can be controlled, and thereby the resolution is improved, change of sensitivity after exposure can be suppressed, dependency on the substrate or environment can be lowered, and exposure margin, pattern profile or the like can be improved.

Examples of such a basic compound may include: a primary, secondary and tertiary aliphatic amines, a hybrid amine, an aromatic amine, a heterocyclic amine, a compound containing nitrogen which has a carboxyl group, a compound containing nitrogen which has a sulfonyl group, a compound containing nitrogen which has a hydroxyl group, a compound containing nitrogen which has a hydroxy phenyl group, an alcoholic compound containing nitrogen, an amide derivative, an imido derivative and the like.

Illustrative examples of the primary aliphatic amine may include: ammonia, methylamine, ethylamine, n-propylamine, isopropylamine, n-butylamine, isobutyl amine, sec-butyl amine, tert-butylamine, pentylamine, tert-amylamine, cyclopentyl amine, hexylamine, cyclohexyl amine, heptylamine, octylamine, nonylamine, decyl amine, dodecylamine, cetylamine, methylene diamine, ethylenediamine, tetraethylene pentamine and the like. Examples of the secondary aliphatic amine may include: dimethylamine, diethylamine, di-n-propylamine, diisopropyl amine, di-n-butylamine, diisobutyl amine, di-sec-butylamine, dipentylamine, dicyclopentyl amine, dihexyl amine, dicyclohexyl amine, diheptylamine, dioctylamine, dinonylamine, didecylamine, didodecylamine, dicetylamine, N,N-dimethyl methylenediamine, N,N-dimethyl ethylenediamine, N,N-dimethyl tetraethylene pentamine and the like. Examples of the tertiary aliphatic amine may include: trimethylamine, triethylamine, tri-n-propylamine, triisopropyl amine, tri-n-butyl amine, triisobutyl amine, tri-sec-butyl amine, tripentyl amine, tricyclopentyl amine, trihexyl amine, tricyclohexyl amine, triheptyl amine, trioctyl amine, trinonyl amine, tridecyl amine, tridodecyl amine, tricetyl amine, N,N,N',N'-tetra methyl methylene diamine, N,N,N',N'-tetramethyl ethylenediamine, N,N,N',N'-tetramethyl tetraethylene pentamine and the like.

Examples of the mixed amines include: dimethylethyl amine, methylethylpropyl amine, benzyl amine, phenethyl amine, benzyl dimethyl amine and the like.

Examples of the aromatic amines and the heterocyclic amines may include: an aniline derivative (for example, aniline, N-methyl aniline, N-ethyl aniline, N-propyl aniline, N,N-dimethylaniline, 2-methyl aniline, 3-methyl aniline, 4-methyl aniline, ethyl aniline, propyl aniline, trimethyl aniline, 2-nitroaniline, 3-nitroaniline, 4-nitroaniline, 2,4-dinitro aniline, 2,6-dinitro aniline, 3,5-dinitro aniline, N,N-dimethyl toluidine and the like), diphenyl (p-tolyl)amine, methyl diphenylamine, triphenylamine, phenylenediamine, naphthylamine, diamino naphthalene, a pyrrole derivative (for example, pyrrole, 2H-pyrrole, 1-methylpyrrole, 2,4-dimethylpyrrole, 2,5-dimethylpyrrole, N-methylpyrrole, and the like), oxazole derivatives (for example, oxazole, isoxazole and the like), a thiazole derivative (for example, thiazole, isothiazole, and the like), an imidazole derivative (for example, imidazole, 4-methyl imidazole, 4-methyl-2-phenyl imidazole and the like), a pyrazole derivative, a furazan derivative, a pyrroline derivative (for example, pyrroline, 2-methyl-1-pyrroline and the like), a pyrrolidine derivative (for example, pyrrolidine, N-methylpyrrolidine, pyrrolidinone, N-methylpyrolidone and the like), an imidazoline derivative, an imidazolidine derivative, a pyridine derivative (for example, pyridine, methylpyridine, ethyl pyridine, propyl pyridine, butyl pyridine, 4-(1-butyl pentyl) pyridine, dimethylpyridine, trimethylpyridine, triethyl pyridine, phenyl pyridine, 3-methyl-2-phenyl pyridine, 4-tert-butyl pyridine, diphenyl pyridine, benzyl pyridine, methoxy pyridine, butoxy pyridine, dimethoxy pyridine, 1-methyl-2-pyridone, 4-pyrrolidino pyridine, 1-methyl-4-phenyl pyridine, 2-(1-ethylpropyl)pyridine, amino pyridine, dimethyl amino pyridine and the like), a pyridazine derivative, a pyrimidine derivative, a pyrazine derivative, a pyrazoline derivative, a pyrazolidine derivative, a piperidine derivative, a piperazine derivative, a morpholine derivative, an indole derivative, an isoindole derivative, a 1H-indazole derivative, an indoline derivative, a quinoline derivative (for example, quinoline, 3-quinoline carbonitrile, and the like), an isoquinoline derivative, a cinnoline derivative, a quinazoline derivative, a quinoxaline derivative, a phthalazine derivative, a purine derivative, a pteridine derivative, a carbazole derivative, a phenanthridine derivative, an acridine derivative, a phenazine derivative, 1,10-phenanthroline derivative, an adenine derivative, an adenosine derivative, a guanine derivative, a guanosine derivative, a uracil derivative, a uridine derivative and the like.

Furthermore, examples of the compound containing nitrogen which has a carboxy group may include: aminobenzoic acid, indole carboxylic acid, and an amino acid derivative (for example, nicotinic acid, alanine, arginine, aspartic acid, glutamic acid, glycine, histidine, isoleucine, glycyl leucine, leucine, methionine, phenylalanine, threonine, lysine, 3-aminopyrazine-2-carboxylic acid, methoxy alanine) and the like. Examples of the compound containing nitrogen which has a sulfonyl group may include: 3-pyridine sulfonic acid, p-toluenesulfonic acid pyridinium and the like. Examples of the compound containing nitrogen which has a hydroxyl group, the compound containing nitrogen which has a hydroxy phenyl group, and the alcoholic compound containing nitrogen may include: 2-hydroxy pyridine, amino cresol, 2,4-quinoline diol, 3-Indore methanol hydrate, monoethanolamine, diethanolamine, triethanolamine, N-ethyl diethanolamine, N,N-diethyl ethanolamine, triisopropanol amine, 2,2'-iminodiethanol, 2-amino ethanol, 3-amino-1-propanol, 4-amino-1-butanol, 4-(2-hydroxyethyl)morpholine, 2-(2-hydroxyethyl)pyridine, 1-(2-hydroxyethyl)piperazine, 1-[2-(2-hydroxyethoxy)ethyl]piperazine, piperidine ethanol, 1-(2-hydroxy ethyl)pyrrolidine, 1-(2-hydroxyethyl)-2-pyrrolidinone, 3-piperidinone-1,2-propanediol, 3-pyrrolidino-1,2-propanediol, 8-hydroxy julolidine, 3-quinuclidinol, 3-tropanol, 1-methyl-2-pyrrolidine ethanol, 1-aziridine ethanol, N-(2-hydroxyethyl)phthalimide, N-(2-hydroxyethyl)isonicotinamide, and the like.

Examples of the amide derivative may include: formamide, N-methyl formamide, N,N-dimethylformamide, acetamide, N-methyl acetamide, N,N-dimethylacetamide, propione amide, benzamide, and the like.

Examples of the imido derivative may include: phthalimide, succinimide, maleimide, and the like.

Furthermore, one or more compounds selected from basic compounds represented by following general formula (B)-1 can also be added.

(In the formula, n is 1, 2, or 3. The side chain X may be the same or different, and represent the following general formulae (X)-1 to (X)-3. The side chain Y may be the same or different, and represent a hydrogen atom or a linear, branched or cyclic alkyl group having 1–20 carbon atoms which may contain an ether group or a hydroxyl group. Moreover, X may bond to each other and form a ring.

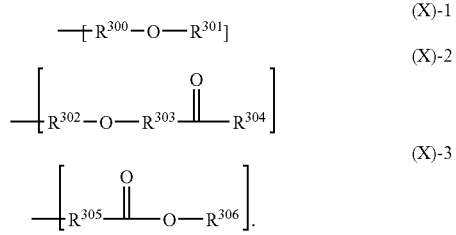

In the formulae, $R^{300}$, $R^{302}$, and $R^{305}$ represent a linear or branched alkylene group having 1–4 carbon atoms, and $R^{301}$ and $R^{304}$ represent a hydrogen atom or a linear, branched or cyclic alkyl group having carbon atoms 1–20, which may contain one or more of a hydroxy group, an ether group, an ester group, and a lactone ring.

$R^{303}$ represents a single bond, or a linear or branched alkylene group having 1–4 carbon atoms, $R^{306}$ represents a linear, branched or cyclic alkyl group having 1–20 carbon atoms, which may contain one or more of a hydroxy group, an ether group, an ester group, and a lactone ring.

Specific examples of the compound represented by the general formula (B)-1 may be as follows:

Tris(2-methoxy methoxy ethyl)amine, tris{2-(2-methoxyethoxy)ethyl}amine, tris{2-(2-methoxy ethoxy methoxy)ethyl} amine, tris{2-(1-methoxyethoxy)ethyl}amine, tris{2-(1-ethoxy ethoxy)ethyl}amine, tris{2-(1-ethoxy propoxy)ethyl}amine, tris[2-{2-(2-hydroxy ethoxy)ethoxy}ethyl] amine, 4,7,13,16,21,24-hexaoxa-1,10-diazabicyclo[8.8.8] hexacosane, 4,7,13,18-tetraoxa-1,10-diazabicyclo[8.5.5] eicosane, 1,4,10,13-tetraoxa-7,16-diazabicyclo octadecane, 1-aza-12-crown-4,1-aza-15-crown-5,1-aza-18-crown-6, tris (2-formyloxyethyl)amine, tris(2-acetoxy ethyl)amine, tris (2-propionyloxyethyl)amine, tris(2-butylyloxyethyl)amine, tris(2-isobutyryloxyethyl)amine, tris(2-valeryloxyethyl) amine, tris(2-pivaloyloxyethyl)amine, N,N-bis(2-acetoxy ethyl)2-(acetoxyacetoxy)ethylamine, tris(2-methoxycarbonyloxyethyl)amine, tris(2-tert-butoxy carbonyloxyethyl) amine, tris[2-(2-oxo propoxy)ethyl]amine, tris[2-(methoxy-carbonyl methyl)oxyethyl]amine, tris[2-(tert-butoxycarbonylmethyloxy)ethyl]amine, tris[2-(cyclohexyloxy carbonylmethyloxy)ethyl]amine, tris(2-methoxycarbonyl ethyl)amine, tris(2-ethoxy carbonyl ethyl) amine, N,N-bis(2-hydroxy ethyl)2-(methoxycarbonyl) ethylamine, N,N-bis(2-acetoxy ethyl)2-(methoxycarbonyl) ethylamine, N,N-bis(2-hydroxy ethyl)2-(ethoxy carbonyl) ethylamine, N,N-bis(2-acetoxy ethyl)2-(ethoxy carbonyl) ethylamine, N,N-bis(2-hydroxy ethyl)2-(2-methoxy ethoxy carbonyl)ethylamine, N,N-bis(2-acetoxy ethyl)2-(2-methoxy ethoxy carbonyl)ethylamine, N,N-bis(2-hydroxy ethyl) 2-(2-hydroxy ethoxy carbonyl)ethylamine, N,N-bis(2-acetoxy ethyl)2-(2-acetoxy ethoxy carbonyl)ethylamine, N,N-bis(2-hydroxy ethyl)2-[(methoxycarbonyl) methoxycarbonyl]ethylamine, N,N-bis(2-acetoxy ethyl)2-[(methoxycarbonyl)methoxycarbonyl]ethylamine, N,N-bis (2-hydroxy ethyl)2-(2-oxo propoxy carbonyl)ethylamine, N,N-bis(2-acetoxy ethyl)2-(2-oxo propoxy carbonyl)ethylamine, N,N-bis(2-hydroxy ethyl)2-(tetrahydrofurfuryloxycarbonyl)ethylamine, N,N-bis(2-acetoxy ethyl)2-(tetrahydrofurfuryloxycarbonyl)ethylamine, N,N-bis(2-hydroxy ethyl)2-[(2-oxotetrahydrofuran-3-yl)oxycarbonyl]ethylamine, N,N-bis(2-acetoxy ethyl)2-[(2-oxotetrahydrofuran-3-yl)oxycarbonyl]ethylamine, N,N-bis(2-hydroxyethyl)2-(4-hydroxy butoxy carbonyl)ethylamine, N,N-bis(2-formyloxyethyl)2-(4-formyloxybutoxy carbonyl) ethylamine, N,N-bis(2-formyloxyethyl)2-(2-formyloxy ethoxy carbonyl)ethylamine, N,N-bis(2-methoxy ethyl)2-(methoxycarbonyl)ethylamine, N-(2-hydroxy ethyl)bis[2-(methoxycarbonyl)ethyl]amine, N-(2-acetoxy ethyl)bis[2-(methoxycarbonyl)ethyl]amine, N-(2-hydroxy ethyl)bis[2-(ethoxy carbonyl)ethyl]amine, N-(2-acetoxy ethyl)bis[2-(ethoxy carbonyl)ethyl]amine, N-(3-hydroxy-1-propyl)bis [2-(methoxycarbonyl)ethyl]amine, N-(3-acetoxy-1-propyl) bis[2-(methoxycarbonyl)ethyl]amine, N-(2-methoxy ethyl) bis[2-(methoxycarbonyl)ethyl]amine, N-butylbis[2-(methoxycarbonyl)ethyl]amine, N-butylbis[2-(2-methoxy ethoxy carbonyl)ethyl]amine, N-methyl bis(2-acetoxy ethyl) amine, N-ethyl bis(2-acetoxy ethyl)amine, N-methyl bis(2-pivaloyloxyethyl)amine, N-ethyl bis[2-(methoxy carbonyloxycarbonyloxy)ethyl]amine, N-ethyl bis[2-(tert-butoxycarbonyloxy)ethyl]amine, tris(methoxycarbonyl methyl)amine, tris(ethoxy carbonyl methyl)amine, N-butyl bis(methoxycarbonyl methyl)amine, N-hexyl bis(methoxycarbonyl methyl)amine, and a β-(diethylamino)-δ-valerolactone. However they are not limited thereto.

Furthermore, one or more kinds of a basic compound with a cyclic structure represented in following general formula (B)-2 can also be added.

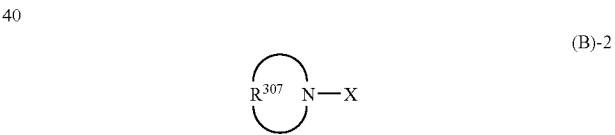

(In the formula, X represents the same as explained above, and $R^{307}$ represents a linear or branched alkylene group having 2–20 carbon atoms, which may contain one or more of a carbonyl group, an ether group, an ester group, or a sulfide.)

Illustrative examples of (B)-2 may include: 1-[2-(methoxy methoxy)ethyl]pyrrolidine, 1-[2-(methoxy methoxy) ethyl]piperidine, 4-[2-(methoxy methoxy)ethyl]morpholine, 1-[2-[(2-methoxyethoxy)methoxy]ethyl]pyrrolidine, 1-[2-[(2-methoxyethoxy)methoxy]ethyl]piperidine, 4-[2-[(2-methoxyethoxy)methoxy]ethyl] morpholine, 2-(1-pyrrolidinyl)ethyl acetate, 2-piperidino ethyl acetate, 2-morpholino ethyl acetate, 2-(1-pyrrolidinyl)ethyl formate, 2-piperidino ethyl propionate, 2-morpholino ethyl acetoxy acetate, 2-(1-pyrrolidinyl)ethyl methoxy acetate, 4-[2-(methoxycarbonyloxy)ethyl]morpholine, 1-[2-(t-butoxycarbonyloxy)ethyl]piperidine, 4-[2-(2-methoxyethoxycarbonyloxy)ethyl] morpholine, methyl 3-(1-pyrrolidinyl)propionate, methyl 3-piperidino propionate, methyl 3-morpholino propionate, methyl 3-(thiomorpholino)propionate, methyl 2-methyl 3-(1-pyrrolidinyl)propionate, ethyl 3-morpholino propionate, methoxycarbonyl methyl 3-piperidino propionate, 2-hydroxy ethyl 3-(1-pyrrolidinyl)propionate, 2-acetoxy ethyl 3-morpholino propionate, 2-oxo tetrahydrofuran-3-yl 3-(1-pyrrolidinyl)propionate, tetra hydro furfuryl 3-morpholino propionate, glycidyl 3-piperidino propionate, 2-methoxy ethyl 3-morpholino propionate, 2-(2-methoxyethoxy)ethyl 3-(1-pyrrolidinyl)propionate, butyl 3-morpholino propionate, cyclohexyl 3-piperidino propionate, α-(1-pyrrolidinyl)methyl-γ-butyrolactone, β-piperidino-γ-butyrolactone, β-morpholino-δ-valerolactone, methyl 1-pyrrolidinyl acetate, methyl piperidino acetate, methyl morpholino acetate, methyl thio morpholino acetate, ethyl 1-pyrrolidinyl acetate, 2-methoxy ethyl morpholino acetate, and the like.

Furthermore, the basic compound containing a cyano group represented by the general formulae (B)-3 to (B)-6 can be added.

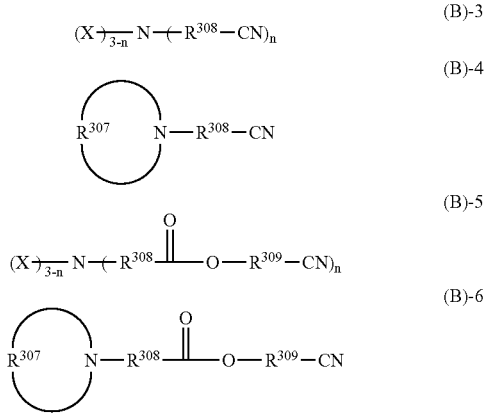

(In the formulae, X, $R^{307}$, and n are the same as explained above, and $R^{308}$ and $R^{309}$ are the same or different and represent a linear or branched alkylene group having 1–4 carbon atoms.)

Illustrative examples of the basic compound containing a cyano group include: 3-(diethylamino)propiononitrile, N,N-bis(2-hydroxy ethyl)-3-amino propiononitrile, N,N-bis(2-acetoxy ethyl)-3-amino propiononitrile, N,N-bis(2-formyl oxy-ethyl)-3-amino propiononitrile, N,N-bis(2-methoxy ethyl)-3-amino propiononitrile, N,N-bis[2-(methoxy methoxy)ethyl]-3-amino propiononitrile, methyl N-(2-cyanoethyl)-N-(2-methoxy ethyl)-3-amino propionate, methyl N-(2-cyanoethyl)-N-(2-hydroxy ethyl)-3-amino propionate, methyl N-(2-acetoxy ethyl)-N-(2-cyanoethyl)-3-amino propionate, N-(2-cyanoethyl)-N-ethyl-3-amino propiononitrile, N-(2-cyanoethyl)-N-(2-hydroxy ethyl)-3-amino propiononitrile, N-(2-acetoxy ethyl)-N-(2-cyanoethyl)-3-amino propiononitrile, N-(2-cyanoethyl)-N-(2-formyl oxyethyl)-3-amino propiononitrile, N-(2-cyanoethyl)-N-(2-methoxy ethyl)-3-amino propiononitrile, N-(2-cyanoethyl)-N-[2-(methoxy methoxy)ethyl]-3-amino propiononitrile, N-(2-cyanoethyl)-N-(3-hydroxy-1-propyl)-3-amino propiononitrile, N-(3-acetoxy-1-propyl)-N-(2-cyanoethyl)-3-amino propiononitrile, N-(2-cyanoethyl)-N-(3-formyloxy-1-propyl)-3-amino propiononitrile, N-(2-cyanoethyl)-N-tetra hydro furfuryl-3-amino propiononitrile, N,N-bis(2-cyanoethyl)-3-amino propiononitrile, diethyl amino acetonitrile, N,N-bis(2-hydroxy ethyl)amino acetonitrile, N,N-bis(2-acetoxy ethyl)amino acetonitrile, N,N-bis(2-formyloxyethyl)amino acetonitrile, N,N-bis(2-methoxy ethyl)amino acetonitrile, N,N-bis[2-(methoxy methoxy)ethyl]amino acetonitrile, methyl N-cyanomethyl-N-(2-methoxy ethyl)-3-amino propionate, methyl N-cyanomethyl-N-(2-hydroxy ethyl)-3-amino propionate, methyl N-(2-acetoxy ethyl)-N-cyanomethyl-3-amino propionate, N-cyanomethyl-N-(2-hydroxy ethyl)amino acetonitrile, N-(2-acetoxy ethyl)-N-(cyanomethyl)amino acetonitrile, N-cyanomethyl-N-(2-formyloxyethyl)amino acetonitrile, N-cyanomethyl-N-(2-methoxy ethyl)amino acetonitrile, N-cyanomethyl-N-[2-(methoxy methoxy)ethyl]amino acetonitrile, N-(cyanomethyl)-N-(3-hydroxy-1-propyl)amino acetonitrile, N-(3-acetoxy-1-propyl)-N-(cyanomethyl)amino acetonitrile, N-cyanomethyl-N-(3-formyloxy-1-propyl)amino acetonitrile, N,N-bis(cyanomethyl)amino acetonitrile, 1-pyrrolidine propiononitrile, 1-piperidine propiononitrile, 4-morpholine propiononitrile, 1-pyrrolidine acetonitrile, 1-piperidine acetonitrile, 4-morpholine acetonitrile, cyanomethyl 3-diethyl amino propionate, cyanomethyl N,N-bis(2-hydroxyethyl)-3-amino propionate, cyanomethyl N,N-bis(2-acetoxy ethyl)-3-amino propionate, cyanomethyl N,N-bis(2-formyloxy-ethyl)-3-amino propionate, cyanomethyl N,N-bis(2-methoxy ethyl)-3-amino propionate, cyanomethyl N,N-bis[2-(methoxy methoxy)ethyl]-3-amino propionate, (2-cyanoethyl)3-diethyl amino propionate, (2-cyanoethyl) N,N-bis(2-hydroxy ethyl)-3-amino propionate, (2-cyanoethyl) N,N-bis(2-acetoxyethyl)-3-amino propionate, (2-cyanoethyl) N,N-bis(2-formyloxyethyl)-3-amino propionate, (2-cyanoethyl) N,N-bis(2-methoxy ethyl)-3-amino propionate, (2-cyanoethyl) N,N-bis[2-(methoxy methoxy)ethyl]-3-amino propionate, cyanomethyl 1-pyrrolidine propionate, cyanomethyl 1-piperidine propionate, cyanomethyl 4-morpholine propionate, (2-cyanoethyl)1-pyrrolidine propionate, (2-cyanoethyl)1-piperidine propionate, (2-cyanoethyl)4-morpholine propionate, and the like.

The blending amount of the basic compound in the resist composition of the present invention is preferably 0.001 to 2 parts, especially 0.01 to 1 parts to 100 parts (parts by weight) of the total base resin. If the amount is fewer than 0.001 parts, the effects achieved by blending are small. If the blending amount is more than 2 parts, sensitivity may be lowered too much.

As a compound which can be added into the resist composition of the present invention and has the group represented by ≡C—COOH in the molecule, one or more kinds of compounds selected, for example from the following I group and II group can be used, but it is not limited thereto. PED (Post Exposure Delay) stability of a resist is improved, and edge roughness on a nitride board is improved by blending the component.

[I Group]

The compounds wherein some or all hydrogen atoms of phenolic hydroxyl groups of the compound represented by following general formula (A1)–(A10) are substituted with —$R^{401}$—COOH ($R^{401}$ is a linear or branched alkylene group having 1–10 carbon atoms), and a mole ratio of the phenolic hydroxyl group (C) and the group (D) represented by ≡C—COOH in a molecule is as follows: C/(C+D)=0.1 to 1.0.

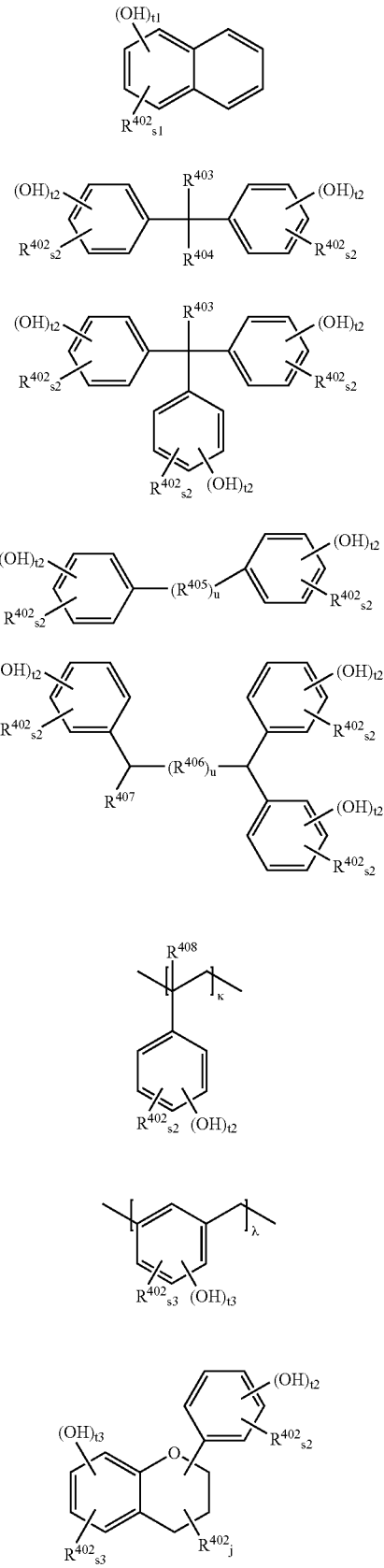

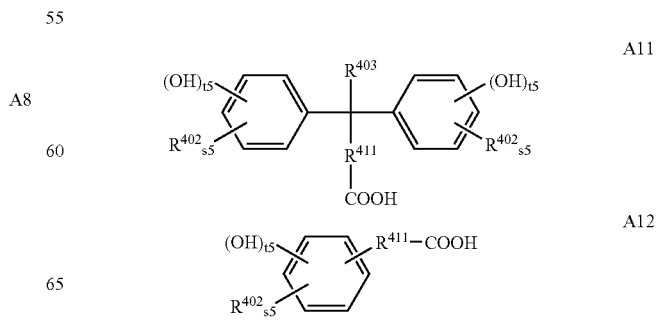

In the formulae, $R^{408}$ represents a hydrogen atom or a methyl group. $R^{402}$ and $R^{403}$ independently represent a hydrogen atom or a linear or branched alkyl group or alkenyl group having 1–8 carbon atoms. $R^{404}$ represents a hydrogen atom, a linear or branched alkyl group or alkenyl group having 1–8 carbon atoms, or —$(R^{409})_h$—COOR' group (R' is a hydrogen atom or —$R^{409}$—COOH). $R^{405}$ represents —$(CH_2)_i$— (i=2–10), an arylene group having 6–10 carbon atoms, a carbonyl group, a sulfonyl group, an oxygen atom, or a sulfur atom. $R^{406}$ represents an alkylene group having 1–10 carbon atoms, an arylene group having 6–10 carbon atoms, a carbonyl group, a sulfonyl group, an oxygen atom, or a sulfur atom. $R^{407}$ represents a hydrogen atom, a linear or branched alkyl group or alkenyl group having 1–8 carbon atoms, or a phenyl group or a naphthyl group substituted with a hydroxyl group. $R^{409}$ represents a linear or branched alkyl group or alkenyl group having 1–10 carbon atoms, or a —$R^{411}$—COOH group. $R^{410}$ represents a hydrogen atom, a linear or branched alkyl group or alkenyl group having 1–8 carbon atoms, or —$R^{411}$—COOH group. $R^{411}$ represents a linear or branched alkylene group having 1–10 carbon atoms. h is an integer of 1–4. j is the number of 0 to 3. Each of s1 to s4 and t1 to t4 satisfies s1+t1=8, s2+t2=5, s3+t3=4, and s4+t4=6, and is the number so that at least one hydroxyl group exists in each phenyl skeleton. u is an integer of 1 to 4. κ is the number so that the weight average molecular weight of the compound represented by the formula (A6) may be 1,000–5,000. λ is the number so that the weight average molecular weight of the compound represented by the formula (A7) may be 1,000–10,000.

[II Group]

The compounds represented by following general formulae (A11)–(A15).

-continued

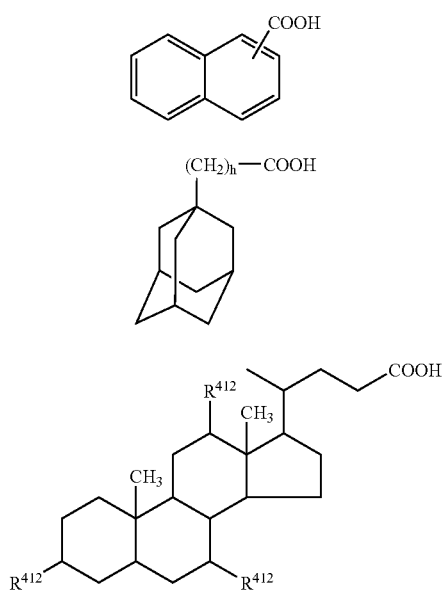

A13

A14

A15

In the formulae, $R^{402}$, $R^{403}$, and $R^{411}$ represent the same meaning as explained above. $R^{412}$ represents a hydrogen atom or a hydroxyl group. s5 and t5 are the number which satisfy: $s5 \geqq 0$, $t5 \geqq 0$, and $s5+t5=5$. h' is 0 or 1.

Illustrative examples of the above compounds may include compounds represented by following general formulae AI-1 to 14 and AII-1 to 10. However, it is not limited thereto.

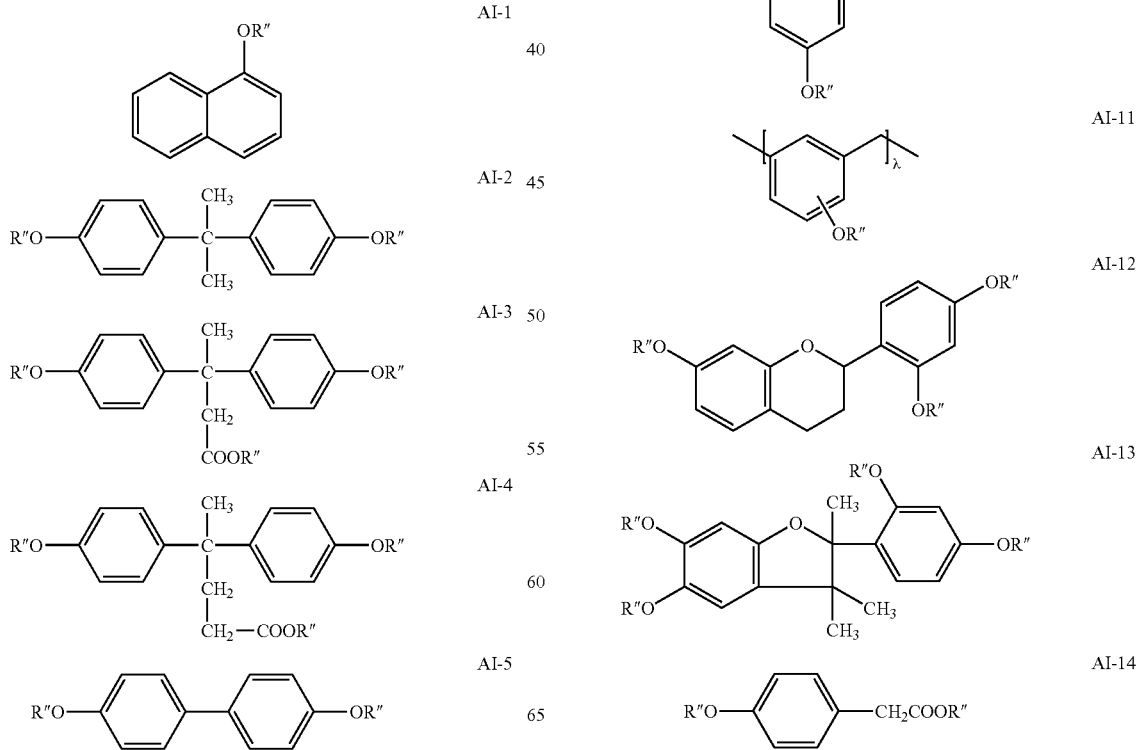

-continued

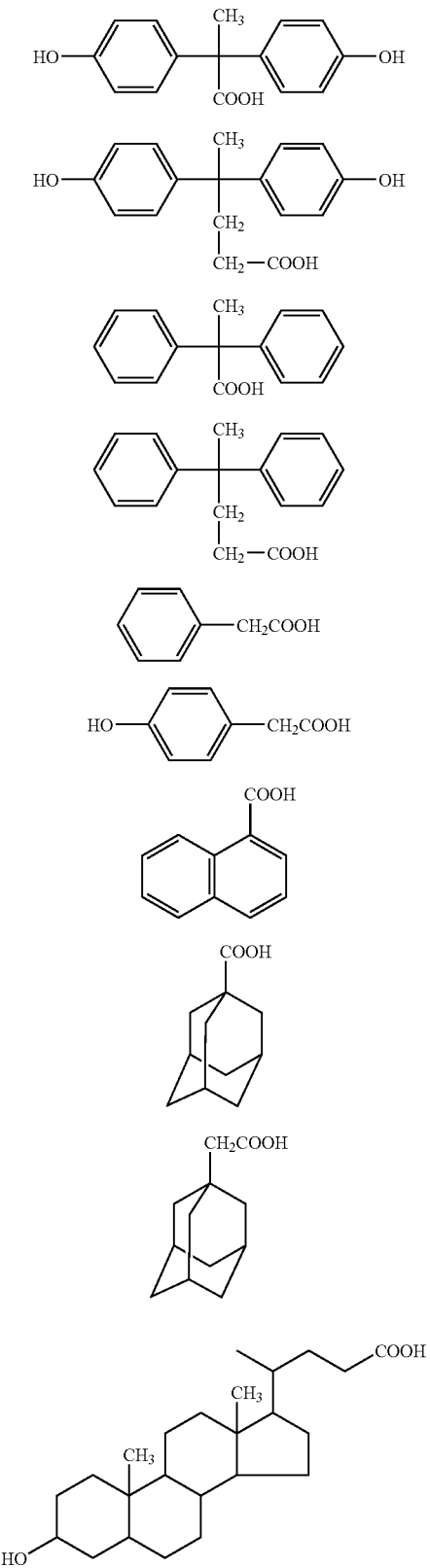

AII-1
AII-2
AII-3
AII-4
AII-5
AII-6
AII-7
AII-8
AII-9
AII-10

In the formulae, R" represents a hydrogen atom or a CH$_2$COOH group, and 10 to 100 mole % of R" is a CH$_2$COOH group in each compound. κ and λ show the same meaning as mentioned above.

An addition amount of the compound which has the group represented by ≡C—COOH in the molecule is 0 to 5 parts, preferably 0.1 to 5 parts, more preferably 0.1 to 3 parts, still more preferably 0.1 to 2 parts to 100 parts (by weight) of the base resin. If it is more than 5 parts, a resolution of the resist composition may be lowered in some cases.

The surfactant for improving an application property or the like can be further added to the positive-resist composition of the present invention, especially chemically amplified positive-resist composition.

The surfactant is not limitative. Examples thereof may include: nonion surfactants such as polyoxyethylene alkyl ethers, such as polyoxyethylene lauryl ether, polyethylene stearyl ether, polyoxyethylene cetyl ether, polyoxyethylene olein ether or the like; polyoxyethylene alkyl allyl ethers such as polyoxyethylene octylphenol ether, polyoxyethylene nonyl phenol or the like; polyoxyethylene polyoxy propylene block copolymers; sorbitan fatty acid esters such as sorbitan monolaurate, sorbitan monopalmitate, sorbitan monostearate or the like; polyoxyethylene sorbitan fatty acid esters such as polyoxyethylene sorbitan monolaurate, polyoxyethylene sorbitan monopalmitate, polyoxyethylene sorbitanmonostearate, polyoxyethylene sorbitan trioleate, polyoxyethylene sorbitan tristearate; fluorinated surfactants such as F-Top EF301, EF303 and EF352 (Tochem Products), Megafac F171, F172, and F173 (manufactured by Dainippon Ink and Chemicals, Inc.), Fluorad FC-430 and FC-431 (manufactured by Sumitomo 3M), Asahiguard AG710, Surflon S-381, S-382, SC101, SC102, SC103, SC104, SC105 and SC106, and Surfynol E1004, KH-10, KH-20, KH-30 and KH-40 (manufactured by Asahi Glass Co., Ltd.), organo siloxane polymer KP-341, X-70-092, X-70-093 (manufactured by Shin-Etsu Chemical Co., Ltd.), acrylic or methacrylic Polyflow No. 75, No. 95 (Kyoei Yushi Kagaku Kogyo), and the like. Preferably, FC430, Surflon S-381, Surfynol E1004, KH-20, and KH-30 are exemplified. These may be used alone or in admixture of two or more of them.

An amount of the surfactant to be added in the positive-resist composition of the present invention, especially chemically amplified positive-resist composition, may be 2 parts by weight or less, preferably one parts by weight or less to 100 parts by weight of solid content in the resist composition.

In the case of using the positive-resist composition of the present invention, especially the chemically amplified positive-resist composition containing organic solvent, the polymer which has one or more of the repeating unit represented by the general formula (1a), the repeating unit represented by the general formula (2a) and the repeating unit represented by the general formula (3b), and the repeating unit represented by the general formula (1c), and an acid generator for manufacture of various integrated circuit, known lithography technology can be used. However, it is not limited thereto.

For example, the substrate for manufacture of integrated circuit (Si, SiO$_2$, SiN, SiON, TiN, WSi, BPSG, SOG, an organic antireflection film, Cr, CrO, CrON, MoSi, or the like) is coated with the resist composition of the present invention, according to an appropriate coating method such as a spin coating, a roll coating, a flow coating, a dip coating, a spray coating, a doctor coating, or the like so that the thickness of the coating film may be 0.1 to 2.0 μm. Next, The coating film is prebaked on a hot plate at 60 to 150° C. for 1 to 10 minutes, preferably at 80–120° C. for 1 to 5 minutes. Subsequently, the intended pattern is exposed through a predetermined mask with light source chosen from ultraviolet ray, far ultraviolet ray, electron beam, X-ray, excimer laser, γ ray, synchrotron-radiation or the like, preferably at an exposure wavelength of 300 nm or less, more preferably at an exposure wavelength in the range of 180 to 200 nm. It is preferable to exposure so that the exposure dose may be about 1–200 mJ/cm$^2$, preferably 10–100 mJ/cm$^2$. Next, post exposure baking (PEB) is conducted at 60–150° C. for 1 to 5 minutes, preferably at 80–120° C. for 1–3 minutes on a hot plate.

Furthermore, the target pattern is preferably formed on a substrate by conducting exposure with a developer of an alkali aqueous solution such as 0.1 to 5%, preferably 2–3% tetramethylammonium hydroxide (TMAH) or the like for 0.1–3 minutes, preferably for 0.5–2 minutes according to a conventional method, such as the dip method, the puddle method, the spray method or the like. In addition, the resist composition of the present invention is suitable for micropatterning especially with a far ultraviolet ray with a wavelength of 254–193 nm, a vacuum ultraviolet ray with a wavelength of 157 nm, electron beam, soft X ray, X-ray, excimer laser, γ ray, synchrotron-radiation, among the high energy beams, preferably with a high energy beam in the range of 180–200 nm.

Moreover, the resist composition of the present invention can also be applied to immersion lithography. In ArF immersion lithography, pure water is used as an immersion solvent. In the immersion lithography, exposure is conducted with inserting water between the resist film after pre-baking and a projection lens. The exposure wavelength is 135 nm which is the value divided by 1.43 as an index of refraction index of water at a wavelength of 193 nm, and it becomes possible to make a wavelength short. It is an important technology for making life time of ArF lithography long as 65 nm node, and the development thereof has been accelerated. The lactone ring which has been used conventionally as a hydrophilic group of ArF resist has a solubility in both an alkali aqueous solution and water. When a lactone with high solubility to water or an acid anhydride such as maleic anhydride or itaconic anhydride are used as a hydrophilic group, water infiltrates from the surface of resist by immersion in water, and the problem of swelling of the resist surface is caused. However, it is considered that influence of dissolution and swelling due to the above-mentioned immersion is small, since hexafluoro alcohol is dissolved in an alkali aqueous solution, but it is not dissolved in water at all.

EXAMPLE

Although Synthetic examples, Comparative synthetic examples, Examples, and Comparative example will be shown and the present invention will be explained concretely hereafter, the present invention is not restricted to the following Examples.

Monomer Synthetic Example 1

300 g of α-(trifluoro methyl)vinyl acetate and 126 g of cyclopentadiene were put into a SUS autoclave with a capacity of 2 L in nitrogen gas flow, and the container was sealed, heated to 160° C., and kept at the temperature for 48 hours. After cooling with ice and lowering the internal pressure, the content was transferred to a 2 L Kjeldahl flask and evaporated under vacuum, to provide 151.4 g of the following compound (M-1). The yield was 35.3%.

150 g of the resultant compounds (M-1) was put into a 3 L 4 neck flask in nitrogen atmosphere, and 585 g of trifluoroacetic acid was dropped little by little therein. Then, 10 g of methansulfonic acid was added further little by little, and the reaction was performed at 70° C. for 6 hours after completion of addition. It was cooled to the room temperature after completion of the reaction, and 1.2 L of hexane was added and then the organic layer was washed twice with a saturated aqueous solution of sodium hydrogencarbonate.

The resultant organic substance obtained by evaporating the organic layer to dryness with an evaporator was dissolved in 1.5 L of methanol, potassium carbonate was added therein, and it was agitated at the room temperature for 10 hours. After removing methanol with an evaporator, the organic substance was dissolved in 1.2 L of ether, and was washed twice with a saturated aqueous solution of sodium chloride. The resultant oily residue was purified by silica gel chromatography. As a result, 90.8 g of the following compound (M-2) was obtained. The yield was 67.9%.

84 g of the compound (M-2), 73.5 g of triethylamine, 0.5 g of phenothiazin and 0.5 g of dimethyl amino pyridine were put into a 3 L Kjeldahl flask under nitrogen atmosphere, and they were dissolved in a mixed solvent of 500 g of dichloromethane and 200 g of tetrahydrofuran. 52.5 g of methacryloyl chloride was dropped therein, after dipping a flask in ice bath. Aging was performed for 5 hours with keeping the flask to be dipped in ice bath. After returning to a room temperature, 800 mL of ether was supplied and then 800 mL of water was added further. The organic layer was washed with an aqueous solution of formic acid, a saturated solution of potassium carbonate and a saturated solution of sodium chloride, and then dried with magnesium sulfate. After concentrated under vacuum with an evaporator, the resultant oily residue was purified by a silica gel chromatography. 83.9 g of Monomer 1 was obtained. The yield was 74.7%.

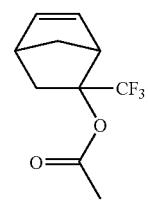

M-1

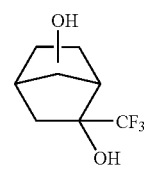

M-2

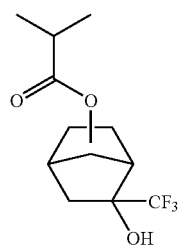

Monomer 1

$^1$H-NMR(DMSO): δ 1.24–2.52 (m, 11H), 4.53 (m, 0.3H), 4.69 (m, 0.7H), 5.66 (t, 1H), 5.97–6.04 (m, 2H) $^{19}$F-NMR (DMSO): δ–79.0 (2.1F), –74.5 (0.9F) FT-IR(KBr):3482, 2981, 1716, 1697, 1633, 1450, 1405, 1386, 1330, 1297, 1222, 1164, 1130, 1103, 1076, 1045, 1012, 981, 971, 948 cm$^{-1}$

Monomer Synthetic Example 2

80 g of the following compound (M-3) obtained by a conventional method such as Nakai et al method (Organic Synthesis, volume 76, page 151, 1998) and 21 g of cyclopentadiene were put into a SUS autoclave with a capacity of 2 L in nitrogen gas flow, and the container was sealed, heated to 160° C., and kept at the temperature for 48 hours. After cooling with ice and lowering the internal pressure, the content was transferred to a 2 L Kjeldahl flask and evaporated under vacuum, to provide 75.4 g of the following compound (M-4). The yield was 74.7%.

70 g of the resultant compound (M-4) was put into a 1 L 4 neck flask in nitrogen atmosphere, the flask was dipped in ice bath, and 220 ml of 1 M borane THF solution was dropped little by little therein. After completion of dropping, the reaction was performed at room temperature for 6 hours. Then, the flask was dipped in ice bath, 5 g of water was dropped therein, 53 ml of 5 N aqueous solution of sodium hydroxide was dropped therein, and 90 ml of hydrogen peroxide was dropped therein. Then, it was taken out from ice bath and aged at a room temperature for 2 hours. Thereafter, the resultant salt was dissolved in 200 ml of water, and then the organic layer was separated. The water layer was extracted with 200 ml of hexane and combined to the organic layer. The organic layer was washed twice with a saturated aqueous solution of sodium sulfite and a saturated aqueous solution of sodium chloride.

The resultant organic substance obtained by drying the organic layer with magnesium sulfate was dissolved in 500 ml of methanol, potassium carbonate was added therein, and it was agitated at the room temperature for 10 hours. After removing methanol with an evaporator, the organic substance was dissolved in 1 L of ether and was washed twice with a saturated aqueous solution of sodium chloride. The resultant oily residue was purified by silica gel chromatography. As a result, 41.5 g of the following compound (M-5) was obtained. The yield was 81.2%.

40 g of the compound (M-5), 29.6 g of triethylamine, 0.2 g of phenothiazin and 0.2 g of dimethyl amino pyridine were put into a 1 L 4 neck flask under nitrogen atmosphere, and they were dissolved in a mixed solvent of 200 g of dichloromethane and 100 g of tetrahydrofuran. After the flask was dipped in ice bath, 20 g of methacryloyl chloride was dropped therein and it was aged for 5 hours with being dipped in ice bath. After returning to a room temperature, 200 mL of ether was put therein and then 300 mL of water was added further. The organic layer was washed with an aqueous solution of formic acid, a saturated aqueous solution of potassium carbonate and a saturated aqueous water of sodium chloride, and then dried with magnesium sulfate. After concentrated under vacuum with an evaporator, the resultant oily residue was purified by a silica gel chromatography. 34.0 g of Monomer 2 was obtained. The yield was 65.7%.

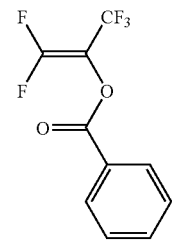

M-3

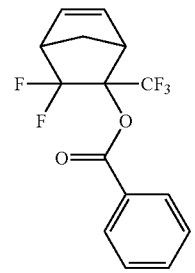

M-4

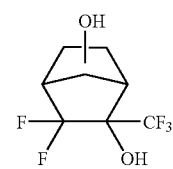

M-5

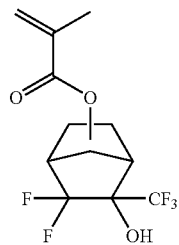

Monomer 2

$^1$H-NMR(DMSO): δ1.44–2.82 (m, 9H), 4.90–5.23 (m, 1H), 5.69–6.06 (m, 2H), 7.01–7.39 (br, Total:1H) $^{19}$F-NMR (DMSO): –118.9–116.3 (Total:1F), –110.6–106.3 (Total: 1F), –72.1, –72.7, –74.6, –75.3 (Total:3F) FT-IR (NaCl): 3598, 3434, 2991, 2933, 1708, 1635. 1454, 1405, 1378, 1313, 1263, 1180, 1135, 1099, 1033, 1010, 991, 956, 939, 921 cm$^{-1}$ Polymer Synthetic Example 1

To 100 mL flask were added 9.8 g of methacrylic acid-2-ethyl-2-adamantane, 4.3 g of methacrylic acid 3-oxo-2,7-dioxatricyclo[4.2.1.0$^{4,8}$]-9-nonyl, and 16.8 g of methacrylic acid 5-hydroxy-5-trifluoromethyl-bicyclo[2.2.1]hept-2-yl (the above-mentioned monomer 1), and 20 g of tetrahydrofuran as a solvent. This reaction container was cooled to –70° C. in nitrogen atmosphere, and deaerating under reduced pressure and flowing of nitrogen gas were repeated 3 times. 0.2 g of AIBN was added as a polymerization initiator after elevating a temperature to a room temperature, and it was allowed to react for 15 hours after elevating a temperature to 60° C. To this reaction solution was added 500 ml of isopropyl alcohol solution, and a white solid was precipitated. The obtained white solid was taken by filtration and then dried under reduced pressure at 60° C., and 23.3 g of white polymer was obtained.

The obtained polymer was analyzed by $^{13}C$, $^{1}H$-NMR and GPC measurement. The following analysis results were obtained.

Copolymerization Ratio methacrylic acid-2-ethyl-2-adamantane:methacrylic acid 3-oxo-2,7-dioxatricyclo[4.2.1.0$^{4,8}$]-9-nonyl:methacrylic acid 5-hydroxy-5-trifluoromethyl-bicyclo[2.2.1]hept-2-yl=0.40:0.14:0.46

Weight average-molecular-weight (Mw)=11,200

Molecular weight distribution (Mw/Mn)=1.78

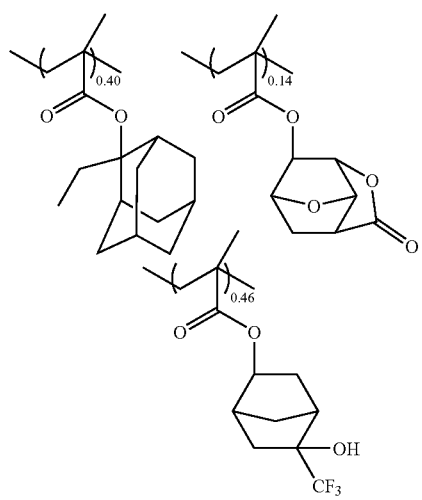

Polymer 1

This polymer is defined as Polymer 1.

Polymer Synthetic Example 2

To 100 mL flask were added 9.8 g of methacrylic acid-2-ethyl-2-adamantane, 10.0 g of methacrylic acid 3-oxo-2,7-dioxa-tricyclo[4.2.1.0$^{4,8}$]-9-nonyl, and 8.8 g of methacrylic acid 5-hydroxy-5-trifluoromethyl-bicyclo[2.2.1]hept-2-yl, and 20 g of tetrahydrofuran as a solvent. This reaction container was cooled to −70° C. in nitrogen atmosphere, and deaerating under reduced pressure and flowing of nitrogen gas were repeated 3 times. 0.2 g of AIBN was added as a polymerization initiator after elevating a temperature to a room temperature, and it was allowed to react for 15 hours after elevating a temperature to 60° C. To this reaction solution was added 500 ml of isopropyl alcohol solution, and a white solid was precipitated. the obtained white solid was taken by filtration and then dried under reduced pressure at 60° C., and 18.3 g of white polymer was obtained.

The obtained polymer was analyzed by $^{13}C$, $^{1}H$-NMR and GPC measurement. The following analysis results were obtained.

Copolymerization Ratio methacrylic acid-2-ethyl-2-adamantane:methacrylic acid 3-oxo-2,7-dioxatricyclo[4.2.1.0$^{4,8}$]-9-nonyl:methacrylic acid 5-hydroxy-5-trifluoromethyl-bicyclo[2.2.1]hept-2-yl=0.38:0.26:0.36

Weight average-molecular-weight (Mw)=10,200

Molecular weight distribution (Mw/Mn)=1.74

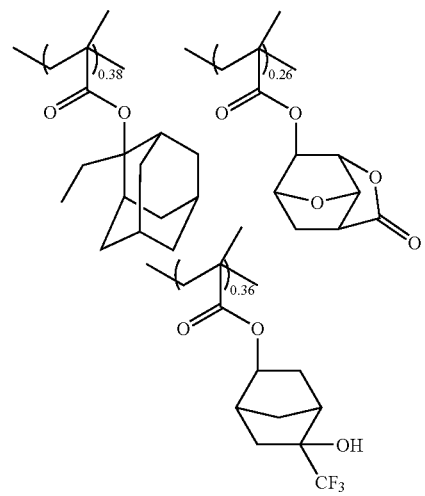

Polymer 2

This polymer is defined as Polymer 2.

Polymer Synthetic Example 3

To 100 mL flask were added 15.8 g of methacrylic acid-1-(1-adamantyl)-1-methylethyl, 4.3 g of methacrylic acid 3-oxo-2,7-dioxa-tricyclo[4.2.1.0$^{4,8}$]-9-nonyl, and 16.8 g of methacrylic acid 5-hydroxy-5-trifluoromethyl-bicyclo[2.2.1]hept-2-yl (the above-mentioned Monomer 1), and 20 g. of tetrahydrofuran as a solvent. This reaction container was cooled to −70° C. in nitrogen atmosphere, and deaerating under reduced pressure and flowing of nitrogen gas were repeated 3 times. 0.2 g of AIBN was added as a polymerization initiator after elevating a temperature to a room temperature, and it was allowed to react for 15 hours after elevating a temperature to 60° C. To this reaction solution was added 500 ml of isopropyl alcohol solution, and a white solid was precipitated. The obtained white solid was taken by filtration and then dried under reduced pressure at 60° C., and 28.3 g of white polymer was obtained.

The obtained polymer was analyzed by $^{13}C$, $^{1}H$-NMR and GPC measurement. The following analysis results were obtained.

Copolymerization Ratio methacrylic acid-1-(1-adamantyl)-1-methylethyl:methacrylic acid 3-oxo-2,7-dioxatricyclo[4.2.1.0$^{4,8}$]-9-nonyl:methacrylic acid 5-hydroxy-5-trifluoromethyl-bicyclo[2.2.1]hept-2-yl=0.40:0.18:0.42

Weight average-molecular-weight (Mw)=9,800

Molecular weight distribution (Mw/Mn)=1.68

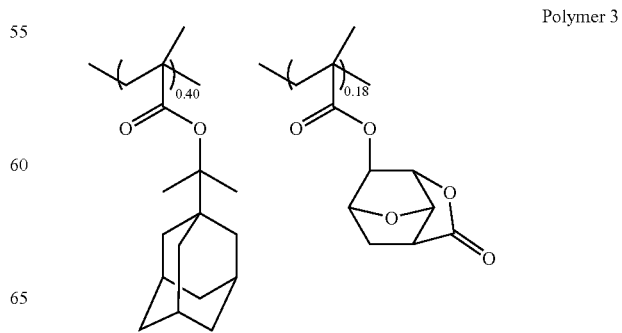

Polymer 3

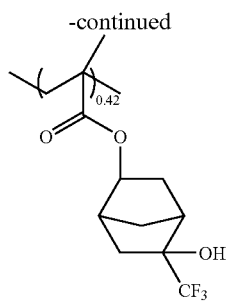

This polymer is defined as Polymer 3.

Polymer Synthetic Example 4

To 100 mL flask were added 12.3 g of methacrylic acid-2-ethyl-2-adamantane, 15.3 g of methacrylic acid 3-oxo-2,7-dioxatricyclo[4.2.1.0$^{4,8}$]-9-nonyl, and 9.3 g of vinyl ether 5-hydroxy-5-trifluoromethyl-bicyclo[2.2.1]hept-2-yl, and 20 g of tetrahydrofuran as a solvent. This reaction container was cooled to −70° C. in nitrogen atmosphere, and deaerating under reduced pressure and flowing of nitrogen gas were repeated 3 times. 0.2 g of AIBN was added as a polymerization initiator after elevating a temperature to a room temperature, and it was allowed to react for 15 hours after elevating a temperature to 60° C. To this reaction solution was added 500 ml of isopropyl alcohol solution, and a white solid was precipitated. The obtained white solid was taken by filtration and then dried under reduced pressure at 60° C., and 22.5 g of white polymer was obtained.

The obtained polymer was analyzed by $^{13}$C, $^{1}$H-NMR and GPC measurement. The following analysis results were obtained.

Copolymerization Ratio
methacrylic acid-2-ethyl-2-adamantane: methacrylic acid 3-oxo-2,7-dioxatricyclo[4.2.1.0$^{4,8}$]-9-nonyl:vinyl ether 5-hydroxy-5-trifluoromethyl-bicyclo[2.2.1]hept-2-yl=0.42:0.38:0.20
Weight average-molecular-weight (Mw)=14,000
Molecular weight distribution (Mw/Mn) 1.98

Polymer 4

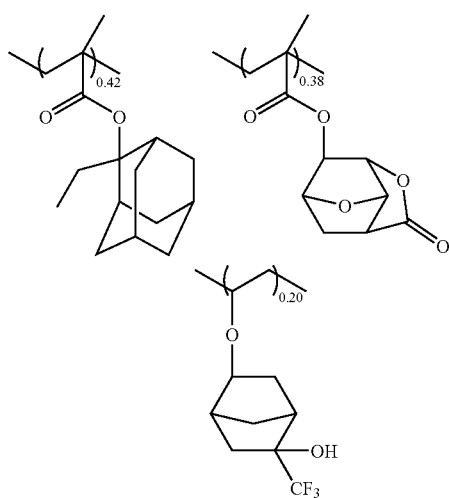

This polymer is defined as Polymer 4.

Polymer Synthetic Example 5

To 100 mL flask were added 12.3 g of methacrylic acid-2-ethyl-2-adamantane, 11.1 g of methacrylic acid 5-oxo-4-oxatricyclo[4.2.1.0$^{3,7}$]nonan-2-yl, and 14.3 g of methacrylic acid 5-hydroxy-5-trifluoromethyl-6,6-difluoro-bicyclo[2.2.1]hept-2-yl (the above-mentioned Monomer 2), and 20 g of tetrahydrofuran as a solvent. This reaction container was cooled to −70° C. in nitrogen atmosphere, and deaerating under reduced pressure and flowing of nitrogen gas were repeated 3 times. 0.2 g of AIBN was added as a polymerization initiator after elevating a temperature to a room temperature, and it was allowed to react for 15 hours after elevating a temperature to 60° C. To this reaction solution was added 500 ml of isopropyl alcohol solution, and a white solid was precipitated. The obtained white solid was taken by filtration and then dried under reduced pressure at 60° C., and 22.5 g of white polymer was obtained.

The obtained polymer was analyzed by $^{13}$C, $^{1}$H-NMR and GPC measurement. The following analysis results were obtained.

Copolymerization Ratio
methacrylic acid-2-ethyl-2-adamantane:methacrylic acid 5-oxo-4-oxatricyclo[4.2.1.0$^{3,7}$]nonan-2-yl:methacrylic acid 5-hydroxy-5-trifluoromethyl-6,6-difluoro-bicyclo[2.2.1]hept-2-yl=0.40:0.40:0.20
Weight average-molecular-weight (Mw)=13,000 Molecular weight distribution (Mw/Mn)=1.78

Polymer 5

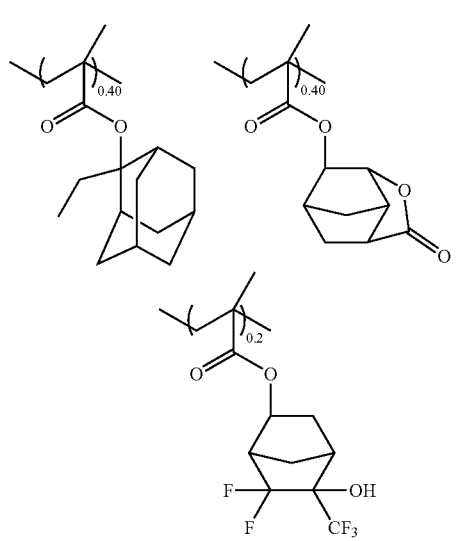

This polymer is defined as Polymer 5.

Polymer synthetic Example 6

To 100 mL flask were added 14.5 g of methacrylic acid-2-adamantyloxy methyl, 11.1 g of methacrylic acid 5-oxo-4-oxa-tricyclo[4.2.1.0$^{3,7}$]nonan-2-yl, and 14.3 g of methacrylic acid 5-hydroxy-5-trifluoromethyl-6,6-difluoro-bicyclo[2.2.1]hept-2-yl (the above-mentioned Monomer 2), and 20 g of tetrahydrofuran as a solvent. This reaction container was cooled to −70° C. in nitrogen atmosphere, and deaerating under reduced pressure and flowing of nitrogen gas were repeated 3 times. 0.2 g of AIBN was added as a polymerization initiator after elevating a temperature to a room temperature, and it was allowed to react for 15 hours after elevating a temperature to 60° C. To this reaction solution was added 500 ml of isopropyl alcohol solution, and a white solid was precipitated. The obtained white solid was taken by filtration and then dried under reduced pressure at 60° C., and 22.5 g of white polymer was obtained.

The obtained polymer was analyzed by $^{13}C$, $^1H$-NMR and GPC measurement. The following analysis results were obtained.

Copolymerization Ratio methacrylic acid-2-adamantyloxy methyl:methacrylic acid 5-oxo-4-oxatricyclo[4.2.1.0$^{3,7}$]nonan-2-yl:methacrylic acid 5-hydroxy-5-trifluoromethyl-6,6-difluoro-bicyclo [2.2.1]hept-2-yl=0.31:0.43:0.26

Weight average-molecular-weight (Mw)=11,500

Molecular weight distribution (Mw/Mn)=1.74

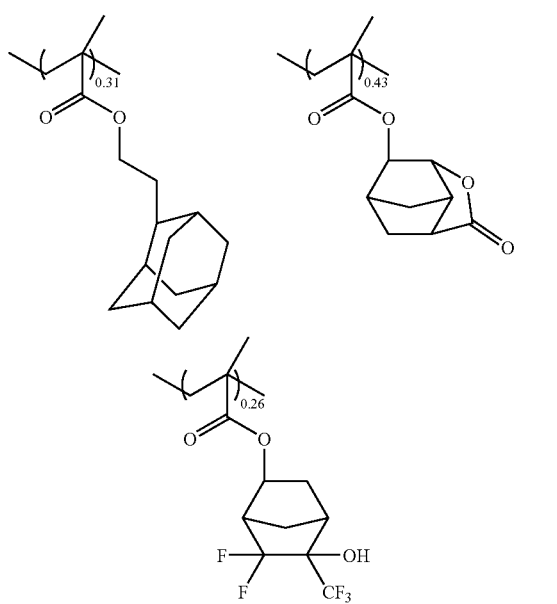

This polymer is defined as Polymer 6.

Polymer Synthetic Example 7

To 100 mL flask were added 12.3 g of methacrylic acid-2-ethyl-2-adamantane, 8.6 g of methacrylic acid methoxy isobutyl, 18.5 g of methacrylic acid-3-hydroxy-1-adamantyl, and 20.5 g of methacrylic acid 5-hydroxy-5-trifluoromethyl-6,6-difluoro-bicyclo[2.2.1]hept-2-yl (the above-mentioned Monomer 2), and 20 g of tetrahydrofuran as a solvent. This reaction container was cooled to −70° C. in nitrogen atmosphere, and deaerating under reduced pressure and flowing of nitrogen gas were repeated 3 times. 0.2 g of AIBN was added as a polymerization initiator after elevating a temperature to a room temperature, and it was allowed to react for 15 hours after elevating a temperature to 60° C. To this reaction solution was added 500 ml of isopropyl alcohol solution, and a white solid was precipitated. The obtained white solid was taken by filtration and then dried under reduced pressure at 60° C., and 22.5 g of white polymer was obtained.

The obtained polymer was analyzed by $^{13}C$, $^1H$-NMR and GPC measurement. The following analysis results were obtained.

Copolymerization Ratio methacrylic acid-2-ethyl-2-adamantane:methacrylic acid methoxy isobutyl:methacrylic acid-3-hydroxy-1-adamantyl:methacrylic acid 5-hydroxy-5-trifluoromethyl-6,6-difluoro-bicyclo[2.2.1]hept-2-yl=0.20:0.10:0.29:0.41

Weight average-molecular-weight (Mw)=9,700

Molecular weight distribution (Mw/Mn)=1.58

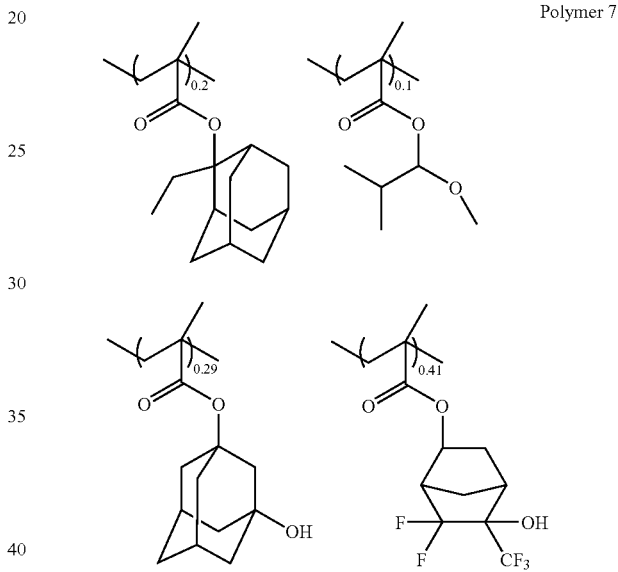

This polymer is defined as Polymer 7.

Comparative Synthetic Example 1

24.4 g of methacrylic acid-2-ethyl-2-adamantane and 17.1 g of methacrylic acid γ butyrolactone, and 40 g of tetrahydrofuran as a solvent were added in 100 mL flask. This reaction container was cooled to −70° C. under nitrogen atmosphere, and deaerating under reduced pressure and flowing of nitrogen gas were repeated 3 times. 0.2 g of AIBN was added as a polymerization initiator after elevating a temperature to a room temperature, and it was allowed to react for 15 hours after elevating a temperature to 60° C. To this reaction solution was added 500 ml of isopropyl alcohol solution, and a white solid was precipitated. The obtained white solid was taken by filtration and then dried under reduced pressure at 60° C., and 36.1 g of white polymer was obtained.

The obtained polymer was analyzed by $^{13}C$, $^1H$-NMR and GPC measurement. The following analysis results were obtained.

Copolymerization Ratio
Methacrylic-acid-2-ethyl-2-adamantane:Methacrylic acid γ butyrolactone=0.48:0.52
Weight average-molecular-weight (Mw)=12500
Molecular weight distribution (Mw/Mn)=1.88

Comparative polymer 1

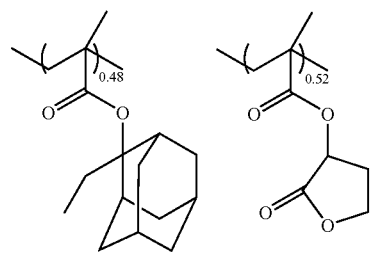

This polymer is referred to as Comparative polymer 1.

Examples, Comparative Examples

[Preparation of Positive-Resist Composition]

Using the polymers (Polymers 1–7, Comparative polymer 1), solutions in which the components were dissolved at composition shown in the following Table 1 were filtered with a 0.2 μm filter to prepare resist solutions.

Each composition in Table 1 is as follows. Polymer 1-Polymer 7: obtained from Synthetic examples 1–7 Comparative Polymer 1: obtained from Comparative Example 1 Acid generator: PAG1 (refer to the following structural formula)

PAG1

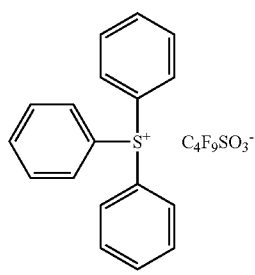

Basic compound: tributyl amine, triethanolamine TMMEA, AAA, and AACN (refer to the following structural formulae)

TMMEA

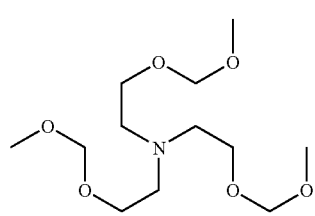

-continued

AAA

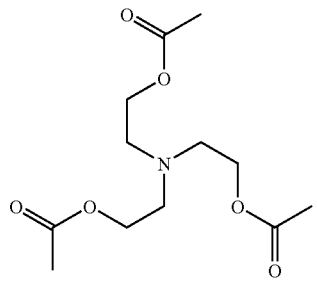

AACN

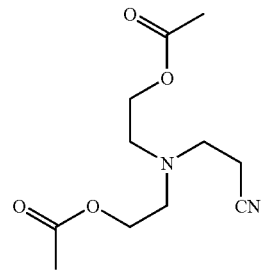

Dissolution inhibitor: DRIL (refer to the following structural formula)

DRI 1

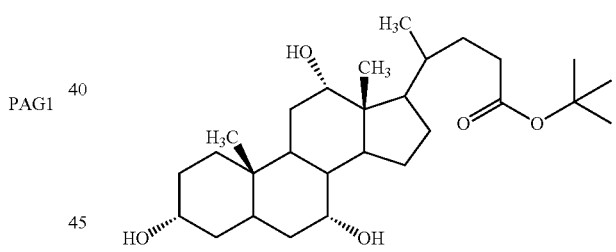

Organic solvent: PGMEA (propyleneglycolmonomethyl-ether acetate)

[Evaluation of Exposure Patterning]

With each of the prepared resist compositions (Examples 1–12, Comparative example 1) was spin-coated substrate wherein film of AR-19 (manufactured by Shipley) with a thickness of 82 nm was formed on silicon wafer. Then, it was baked for 60 seconds at 130° C. using a hot plate, so that a thickness of the resist may be 250 nm.

It was exposed using the ArF excimer laser stepper (NSR-S305B, NA-0.68, σ0.85, ⅔ annular illumination manufactured by Nicon), it was baked at 110° C. for 60 seconds immediately after exposure, development was performed for 60 seconds in 2.38% aqueous solution of tetramethylammonium hydroxide, and thus the positive pattern was obtained.

The obtained resist pattern was evaluated as follows.

Defining the exposure dose which resolves a line and space with 0.12 μm by 1:1 as sensitivity of resist, the minimum line width of the line and space separated in the exposure dose was defined as resolution of the resist to be evaluated.

Moreover, line edge roughness of a line and space with 0.12 μm was measured using the CD-SEM (S-9220 manufactured by Hitachi Seisakusho).

These results were shown together in Table 1.

Figure 2:
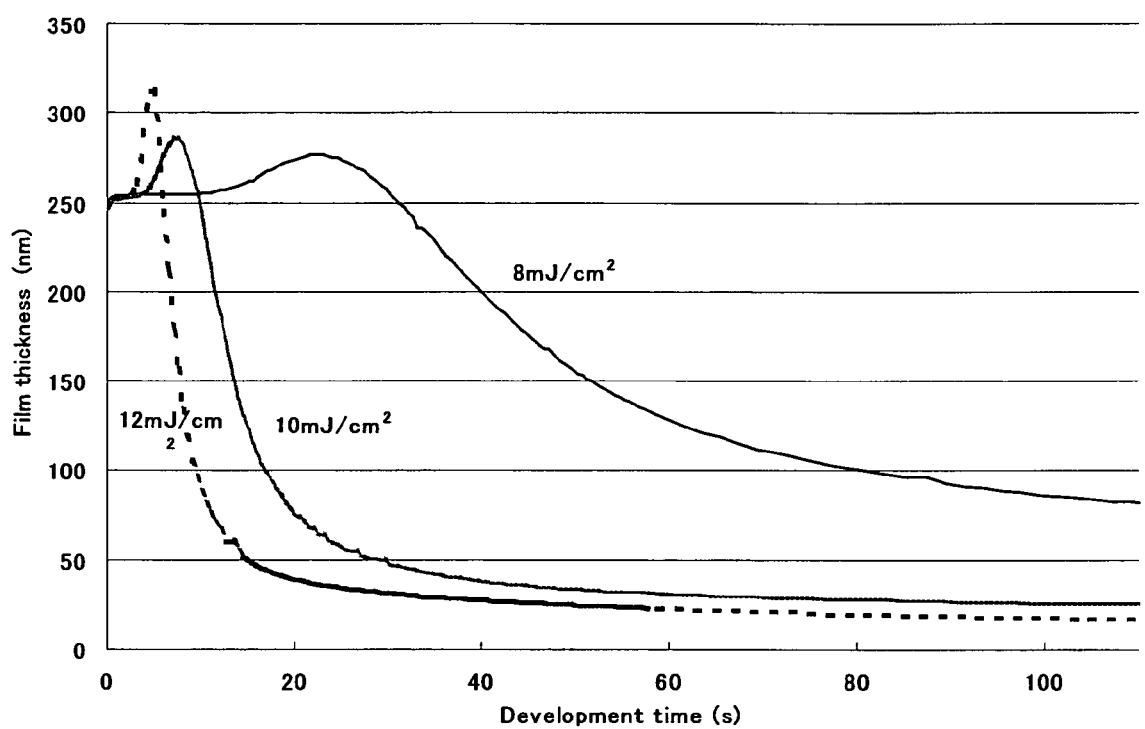
FIG. 2 is a graph which shows the result of the measurement which was performed according to the QCM method as for the resist formed by the resist composition of Comparative Example 1.

These results are shown in FIG. 1 and FIG. 2. In the drawings, a thickness increased to a development time represents swelling, and a thickness decreased thereto represents dissolution.

FIG. 1 and FIG. 2 show that swelling measured by the QCM method during development is suppressed significantly in the resist composition of Example 1.

The present invention is not limited to the above-described embodiments. The above-described embodiments are some examples, and those having the substantially same

TABLE 1

| | Polymer (parts by weight) | Acid Generator (parts by weight) | Basic Compound (parts by weight) | Dissolution Inhibitor (parts by weight) | Organic Solvent (part by weight) | Sensitivity (mJ/cm$^2$) | Resolution (um) | Line Edge Roughness (3σ, nm) |
|---|---|---|---|---|---|---|---|---|
| Example 1 | Polymer 1 (100) | PAG1 (2.2) | Tributyl amine (0.2) | — | PGMEA (800) | 32 | 0.11 | 7.2 |
| Example 2 | Polymer 2 (100) | PAG1 (2.2) | Tributyl amine (0.2) | — | PGMEA (800) | 31 | 0.11 | 6.1 |
| Example 3 | Polymer 3 (100) | PAG1 (2.2) | Tributyl amine (0.2) | — | PGMEA (800) | 35 | 0.11 | 7.8 |
| Example 4 | Polymer4 (100) | PAG1 (2.2) | Tributyl amine (0.2) | — | PGMEA (800) | 28 | 0.11 | 7.9 |
| Example 5 | Polymer 5 (100) | PAG1 (2.2) | Tributyl amine (0.2) | — | PGMEA (800) | 26 | 0.11 | 7.2 |
| Example 6 | Polymer 1 (100) | PAG1 (2.2) | Triethanol amine (0.25) | — | PGMEA (800) | 35 | 0.11 | 7.1 |
| Example 7 | Polymer 1 (100) | PAG1 (2.2) | TMMEA (0.3) | — | PGMEA (800) | 36 | 0.10 | 6.5 |
| Example 8 | Polymer 1 (100) | PAG1 (2.2) | AAA (0.3) | — | PGMEA (800) | 36 | 0.10 | 6.8 |
| Example 9 | Polymer 1 (100) | PAG1 (2.2) | AACN (0.3) | — | PGMEA (800) | 36 | 0.10 | 6.8 |
| Example 10 | Polymer 1 (100) | PAG1 (2.2) | Tributyl amine (0.2) | DRI1 (20) | PGMEA (800) | 28 | 0.11 | 6.3 |
| Example 11 | Polymer 6 (100) | PAG1 (2.2) | TMMEA (0.3) | — | PGMEA (800) | 28 | 0.10 | 5.5 |
| Example 12 | Polymer 7 (100) | PAG1 (2.2) | TMMEA (0.3) | — | PGMEA (800) | 31 | 0.10 | 6.1 |
| Comparative Example 1 | Comparative Polymer 1 (100) | PAG1 (2.2) | Tributyl amine (0.2) | — | PGMEA (800) | 28 | 0.12 | 10.5 |

From Table 1, it is clear that the resist compositions of Examples 1–12 have high sensitivity, high resolution and reduced line edge roughness.

[Evaluation of Dissolution Characteristic in the Developer by the QCM Method]

With each of the resist solutions obtained by filtrating the solutions of the prepared resist compositions (Example 1, Comparative Example 1) with a 0.2 μm filter was spin-coated a quartz board with a size of 1 inch (about 2.5 cm) which has an electrode vapor-depositted with chromium on the surface of a ground made of gold. And it was baked for 60 seconds at 130° C. using a hot plate, to achieve a resist thickness of 250 nm.

It was exposed with the ArF aligner ArFES3000 (manufactured by Litho Tech Japan), and PEB was performed at 115° C. for 60 seconds. The substrate was installed in Quartz resonator micro balance equipment RDA-Qz3 (manufactured by Litho Tech Japan) for resist development analyzers, development was performed for 60 seconds in 2.38% aqueous solution of tetramethylammonium hydroxide, and swelling and dissolution during development were measured by the oscillation mode AT cut. Exposure was performed with changing the exposure dose and QCM was measured.

composition as that described in the appended claims and providing the similar action and effects are included in the scope of the present invention.

What is claimed is:

1. A polymer which has at least one or more of a repeating unit represented by a following general formula (1a), a repeating unit represented by a following general formula (2a) and a repeating unit represented by a following general formula (3b), and a repeating unit represented by a following general formula (1c),

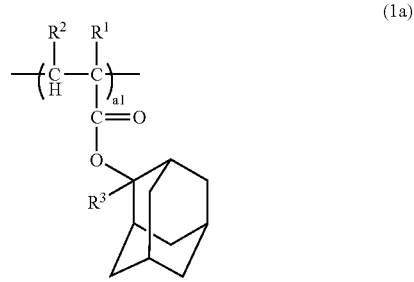

-continued

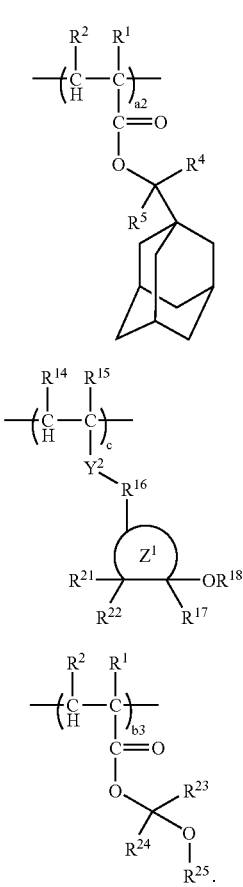

wherein R¹ represents any one of a hydrogen atom, a methyl group and —CH$_2$CO$_2$R$^6$, R² represents any one of a hydrogen atom, a methyl group and —CO$_2$R$^6$, R¹ and R² in the repeating units (1a) and (2a) may be the same or different, R³ to R⁵ each independently represent a monovalent hydrocarbon group having 1–15 carbon atoms which may contain a hetero atom, R⁶ represents a hydrogen atom or a linear, branched or cyclic alkyl group having 1–15 carbon atoms, R¹⁵ represents any one of a hydrogen atom, a methyl group and —CH$_2$CO$_2$R$^6$, R¹⁴ represents any one of a hydrogen atom, a methyl group and —CO$_2$R$^6$, R¹⁶ represents a single bond or a linear or branched alkylene group having 1–4 carbon atoms, R¹⁷ represents a fluorine atom or a trifluoro methyl group, R¹⁸ represents any one of a hydrogen atom, an acyl group having 1–10 carbon atoms and an acid labile group, R²¹ and R²² each independently represent a hydrogen atom or a fluorine atom, R²³ and R²⁴ each independently represent a hydrogen atom or a linear or branched alkyl group having 1–6 carbon atoms, R²⁵ is a linear, branched or cyclic alkyl group having 1–20 carbon atoms, Y² is —O— or —C(=O)—O—, Z¹ is a bridged cyclic hydrocarbon group having 4–10 carbon atoms, which may have —O— and/or —S—, and a1, a2, c, and b3 fall within the range that 0≦a1≦0.8, 0≦a2≦0.8, 0≦b3≦0.8, 0.1≦a1+a2+b3≦0.8, and 0<c≦0.9.

2. The polymer according to claim 1 in which the repeating unit represented by the general formula (1c) is a repeating unit represented by a following general formula,

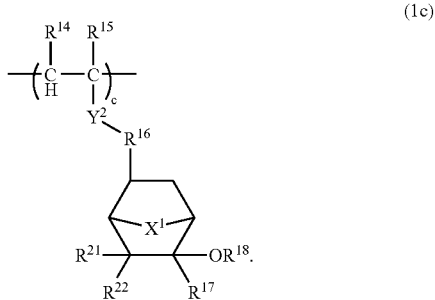

wherein R¹⁴, R¹⁵, R¹⁶, R¹⁷, R¹⁸, R²¹, R²², Y² and c are the same as mentioned above, and X¹ is any one of a methylene group, an ethylene group, an oxygen atom and a sulfur atom.

3. A positive resist composition which contains, at least, the polymer according to claim 2 as a base resin.

4. The positive resist composition according to claim 3 which further contains an organic solvent and an acid generator to serve as a chemically amplified resist composition.

5. The positive resist composition according to claim 4 which further contains a dissolution inhibitor.

6. The positive resist composition according to claim 5 wherein a basic compound and/or a surfactant is further blended as an additive.

7. The positive resist composition according to claim 4 wherein a basic compound and/or a surfactant is further blended as an additive.

8. The positive resist composition according to claim 3 which further contains a dissolution inhibitor.

9. The positive resist composition according to claim 8 wherein a basic compound and/or a surfactant is further blended as an additive.

10. The positive resist composition according to claim 3 wherein a basic compound and/or a surfactant is further blended as an additive.

11. A positive resist composition which contains, at least, the polymer according to claim 1 as a base resin.

12. The positive resist composition according to claim 11 which further contains an organic solvent and an acid generator to serve as a chemically amplified resist composition.

13. The positive resist composition according to claim 11 which further contains a dissolution inhibitor.

14. The positive resist composition according to claim 13 wherein a basic compound and/or a surfactant is further blended as an additive.

15. The positive resist composition according to claim 12 which further contains a dissolution inhibitor.

16. The positive resist composition according to claim 15 wherein a basic compound and/or a surfactant is further blended as an additive.

17. The positive resist composition according to claim 12 wherein a basic compound and/or a surfactant is further blended as an additive.

18. The positive resist composition according to claim 11 wherein a basic compound and/or a surfactant is further blended as an additive.

19. A patterning process comprising, at least, a step of applying the resist composition according to claim 11 to a substrate, a step of conducting heat-treatment, then a step of exposing the applied resist composition with a high energy beam and a step of developing the exposed resist composition by using a developer.

20. The patterning process according to claim 19 wherein the high energy beam has a wavelength in the range of 180 nm–200 nm.

* * * * *